US011446286B1

(12) United States Patent
Elsayed et al.

(10) Patent No.: US 11,446,286 B1
(45) Date of Patent: Sep. 20, 2022

(54) TREATMENT OF FUNGAL INFECTIONS USING DABIGATRAN ETEXILATE

(71) Applicant: KING FAISAL UNIVERSITY, Hofouf (SA)

(72) Inventors: Mahmoud Kandeel Elsayed, Al-Ahsa (SA); Naser Abdullah Alhumam, Al-Ahsa (SA); Abdulla Yousef Al-Taher, Al-Ahsa (SA)

(73) Assignee: KING FAISAL UNIVERSITY, Hofouf (SA)

( * ) Notice: Subject to any disclaimer, the term of this patent is extended or adjusted under 35 U.S.C. 154(b) by 0 days.

(21) Appl. No.: 17/682,107

(22) Filed: Feb. 28, 2022

(51) Int. Cl.
*A61K 31/4439* (2006.01)
*A61P 31/10* (2006.01)

(52) U.S. Cl.
CPC .......... *A61K 31/4439* (2013.01); *A61P 31/10* (2018.01)

(58) Field of Classification Search
CPC ............................ A61K 31/4439; A61P 31/10
See application file for complete search history.

(56) References Cited

U.S. PATENT DOCUMENTS

| | | | | |
|---|---|---|---|---|
| 6,087,380 A | * | 7/2000 | Hauel | C07D 209/14 514/336 |
| 7,932,273 B2 | * | 4/2011 | Schmid | A61P 43/00 546/273.4 |
| 9,034,822 B2 | * | 5/2015 | Van Ryn | A61P 7/02 514/14.1 |
| 9,073,899 B2 | * | 7/2015 | Bartra | C07D 401/12 |
| 9,925,174 B2 | * | 3/2018 | Brauns | A61K 31/4439 |
| 10,335,496 B2 | | 7/2019 | Lannuti et al. | |

FOREIGN PATENT DOCUMENTS

CN 103006512 A 4/2013

OTHER PUBLICATIONS

Stangier, "Clinical pharmacokinetics and pharmacodynamics of the oral direct thrombin inhibitor dabigatran etexilate," Clin. Pharmacokinet., 2008, vol. 47, Issue 5, pp. 285-295.

* cited by examiner

*Primary Examiner* — Timothy R Rozof
(74) *Attorney, Agent, or Firm* — Nath, Goldberg & Meyer; Richard C. Litman

(57) ABSTRACT

A method of treating fungal infections using dabigatran etexilate is provided. The method can include administering a therapeutically effective amount of dabigatran etexilate to a subject in need thereof. In an embodiment, dabigatran etexilate may be effective as a broad-spectrum antifungal agent and may be used to treat infections resulting from a wide array of fungal pathogens. In an embodiment, dabigatran etexilate may be administered to treat either a topical or systemic fungal infection.

8 Claims, 33 Drawing Sheets

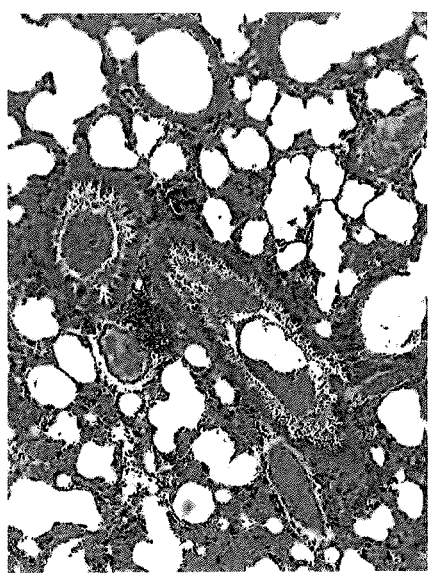 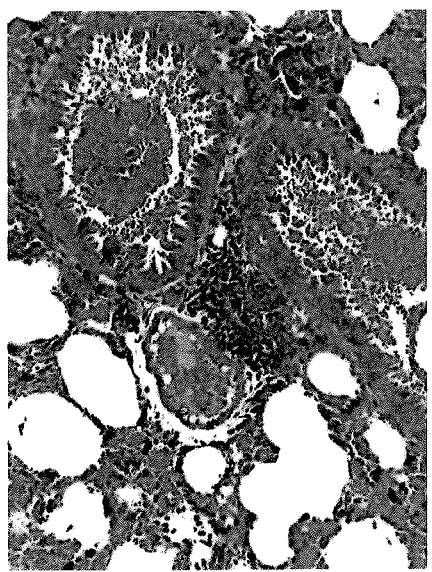
FIG. 7E    FIG. 7F
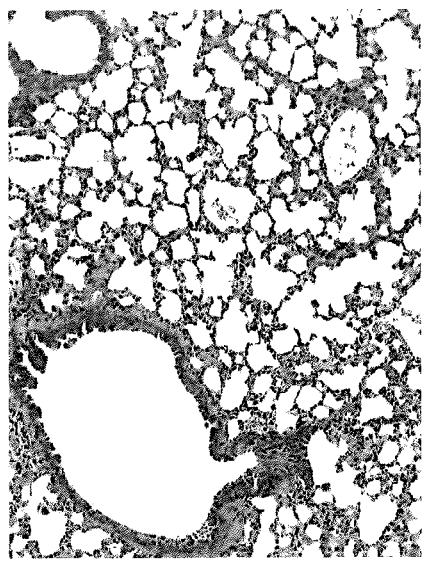 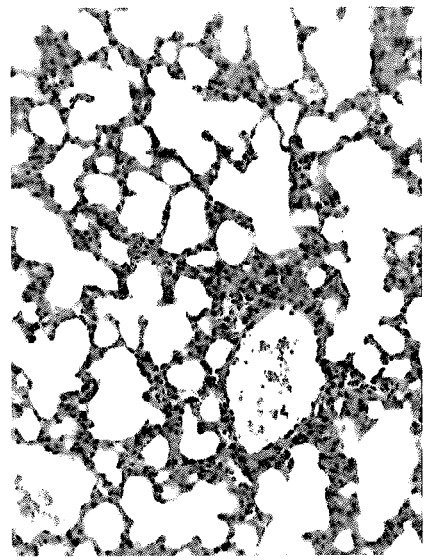
FIG. 7G    FIG. 7H

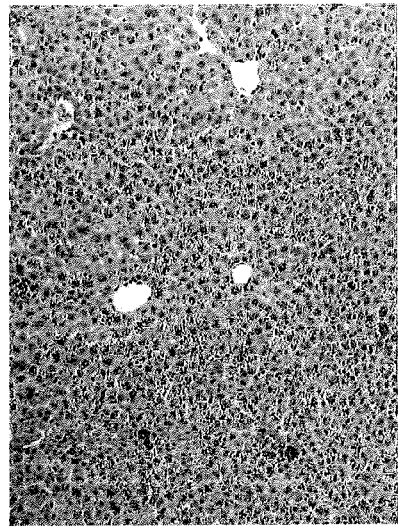 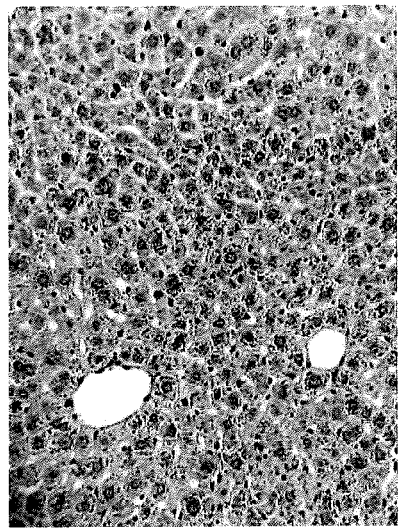
*FIG. 9I*  *FIG. 9J*
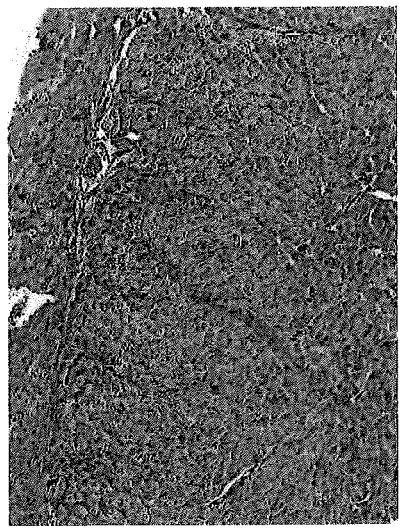 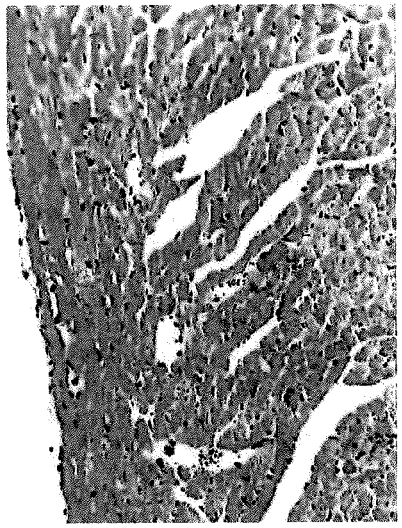
*FIG. 10A*  *FIG. 10B*

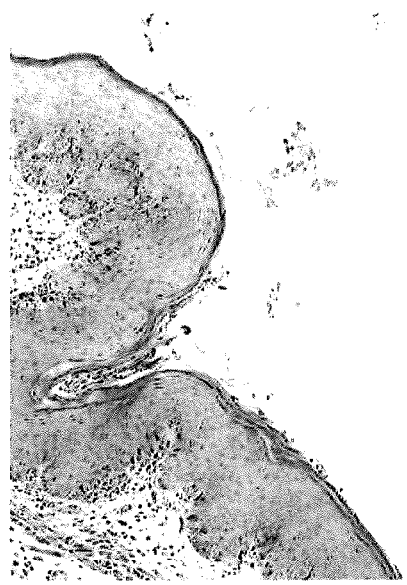
FIG. 14I          FIG. 14J
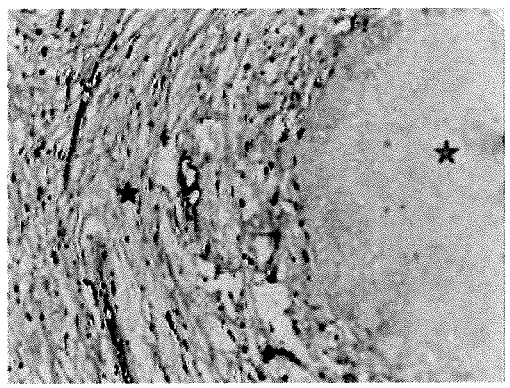
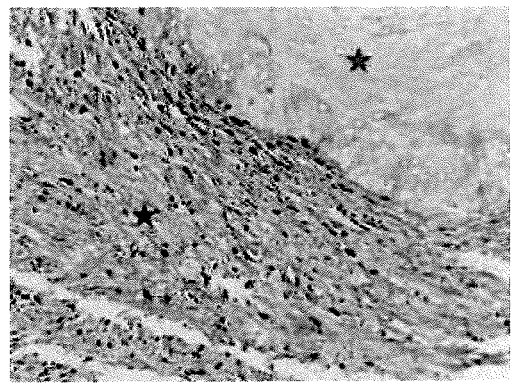
FIG. 15A          FIG. 15B

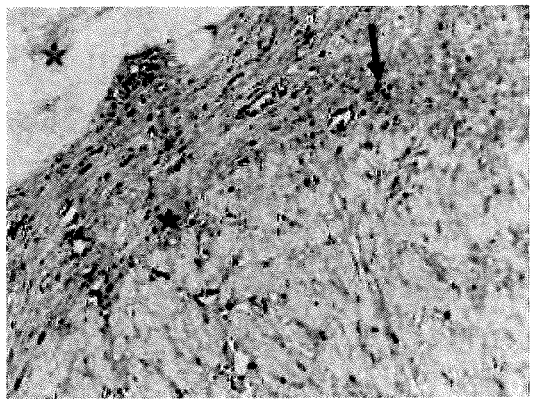
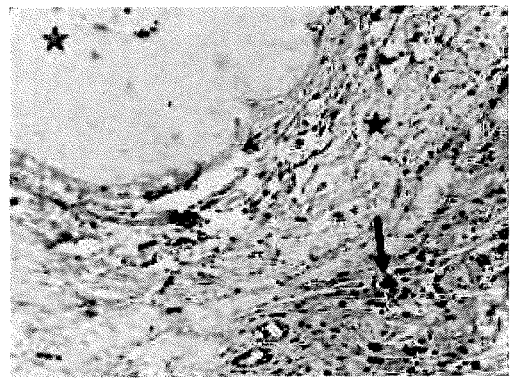
FIG. 18A     FIG. 18B
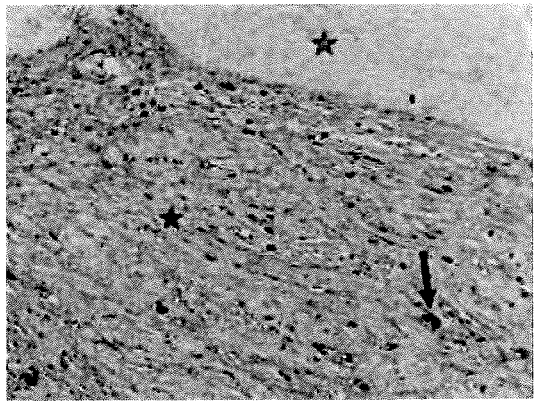
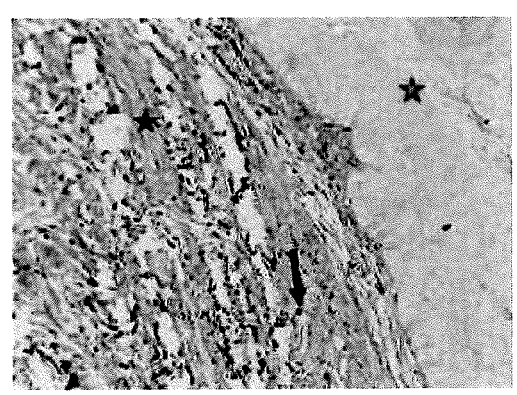
FIG. 19A     FIG. 19B

TREATMENT OF FUNGAL INFECTIONS USING DABIGATRAN ETEXILATE

BACKGROUND

1. Field

The disclosure of the present patent application relates to the treatment of fungal infections and, particularly, to treating fungal infections using dabigatran etexilate.

2. Description of the Related Art

In general, the process of generating new antimicrobials is time-consuming and involves numerous processes. These processes include, for example, target identification and validation, lead identification and validation, and preclinical research with the goal of successfully completing clinical trials. Laboratory procedures, outsourcing approaches, and informatics methodology are included in the biotechnological operations. Drug repurposing helps in speeding up drug discovery by saving time and facilities that would otherwise be directed to trace drug toxicity or clinical aspects (Parvathaneni, V. et al., "Drug repurposing: a promising tool to accelerate the drug discovery process", Drug Discovery Today, 24(10): pp. 2076-2085 (2019)).

Bioinformatics tools have been used heavily in drug discovery research (Kandeel, M. et al., "Virtual screening and repurposing of FDA approved drugs against COVID-19 main protease", Life Sciences, 251:117627 (2020); Kandeel, M. et al., "Discovery of New Fusion Inhibitor Peptides against SARS-CoV-2 by Targeting the Spike S2 Subunit", Biomolecules & Therapeutics. 29(3):282 (2021)). Approaches such as genetic-network mapping, protein-pathway mapping, protein-protein interactions, disease-locus mapping, and subcellular localization predictions can be used for in silico characterization. Preliminary results discovered regarding cellular location and disease/health condition, protein expression, possible binding sites, cross-organism confirmation, or pathways implicated in a disease/health condition may be used to identify a target. Furthermore, increased genomic and proteomic knowledge has enabled the prediction of medication-drug interactions and adverse drug reactions, which is critical in current pharmacology and therapeutics (Rodriguez-Casado, A., "In silico investigation of functional nsSNPs—an approach to rational drug design", Research and Reports in Medicinal Chemistry, 2: pp. 31-42 (2012)).

Fungal pathogens are becoming an even more important cause of disease as the number of people with severely immunocompromised conditions, such as HIV, cancer, and organ transplantation, who are at higher risk for fungal diseases rises. *Candida* species are the most common cause of serious invasive fungal infections. Infections caused by *Cryptococcus, Pneumocystis*, invasive molds, and dimorphic molds also contribute significantly to disease burden (Vallabhaneni S., et al., "The Global Burden of Fungal Diseases," Infectious Disease Clinics of North America, 30(1): pp. 1-11 (2016)). The most prevalent form of invasive fungal disease is *Candida* infection, which is associated with severe morbidity and mortality. Candidemia incidence was recorded from many nations among the general population and in hospital and intensive care unit patients (Vallabhaneni et al.). From 2001 to 2006, invasive aspergillosis accounted for roughly 20 percent of all invasive fungal infections (IFIs), second to invasive candidiasis, among transplant recipients at 23 US transplant facilities (Pappas, P. G., et al., "Invasive Fungal Infections among Organ Transplant Recipients: Results of the Transplant-Associated Infection Surveillance Network (TRANSNET)," Clinical Infectious Diseases, 50(8): pp. 1101-11 (2010)).

Dabigatran etexilate is a prodrug of dabigatran, which is a direct thrombin inhibitor and the most effective physiological activator of platelet aggregation. Dabigatran etexilate binds to thrombin with high affinity and inactivates its biological actions. Because binding is selective, fast, and reversible, its anticoagulant effects should be more predictable than those of irreversible thrombin-binding drugs (Stangier, J., "Clinical pharmacokinetics and pharmacodynamics of the oral direct thrombin inhibitor dabigatran etexilate," Clinical Pharmacokinetics, 47(5): pp. 285-95 (2008)). Thus, dabigatran has been sold by Boehringer Ingelheim under the brand name Pradaxa® for the reduction of stroke risk in nonvalvular atrial fibrillation and to treat deep venous thrombosis and pulmonary embolisms. Dabigatran etexilate is approved for use as an anticoagulant and has been used safely to treat and prevent blood clots and prevent strokes.

Thus, a treatment of fungal infections using dabigatran etexilate is desired.

SUMMARY

A treatment of fungal infections using dabigatran etexilate can include administering a therapeutically effective amount of dabigatran etexilate ($C_{34}H_{41}N_7O_5$) to a subject in need thereof. In an embodiment, the dabigatran etexilate can be administered either topically or systemically. In an embodiment, the subject may be suffering from a fungal infection. In a further embodiment, the fungal infection may result from exposure to one or more of *Aspergillus flavus, Aspergillus fumigatus, Aspergillus nidulans, Aspergillus niger, Aspergillus terreus, Aspergillus ustus, Candida albicans, Candida alibicans, Candida glabrata, Candida lipolytica, Candida tropicalis, Candida tropicalis, Cryptococcus neoformans, Cryptococcus neoformans, Fusarium moniliforme, Geotricum candidum, Microsporum canis, Mucor circillelloides, Penicillium aurantiogriseum, Penicillium expansum, Penicillium italicum, Penicillium marneffei, Penicllium marneffeii, Rhizopus oryzaee, Sporotlirix schenckii, Syncephalastrum racemosum, Trichophyton mentagrophytes,* and *Trichophyton rubrum.*

These and other features of the present subject matter will become readily apparent upon further review of the following specification.

BRIEF DESCRIPTION OF THE DRAWINGS

FIGS. 7A-7J depict histopathological examination of lung sections of healthy control mice (7A-7B), of mice infected with *C. albicans* (7C-7D), of mice infected with *C. albicans* and treated with fluconazole (7E-7F), of mice infected with *C. albicans* and treated with dabigatran etexilate (7G-7H), and of mice infected with *C. albicans* and treated with both fluconazole and dabigatran etexilate (7I-7J). (10×=7A, 7C, 7E, 7G, 7I 40×=7B, 7D, 7F, 7H, 7J)

FIGS. 9A-9J depict histopathological examination of liver sections of healthy control mice (9A-9B), of mice infected with *A. fumigatus* (9C-9D), of mice infected with *A. fumigatus* and treated with fluconazole (9E-9F), of mice infected with *A. fumigatus* and treated with dabigatran etexilate (9G-9H), and of mice infected with *A. fumigatus* and treated with both fluconazole and dabigatran etexilate (9I-9J). (10×=9A, 9C, 9E, 9G, 9I 40×=9B, 9D, 9F, 9H, 9J)

FIGS. 10A-10J depict histopathological examination of heart sections of healthy control mice (10A-10B), of mice infected with *A. fumigatus* (10C-10D), of mice infected with *A. fumigatus* and treated with fluconazole (10E-10F), of mice infected with *A. fumigatus* and treated with dabigatran etexilate (10G-10H), and of mice infected with *A. fumigatus* and treated with both fluconazole and dabigatran etexilate (10I-10J). (10×=10A, 10C, 10E, 10G, 10I 40×=10B, 10D, 10F, 10H, 10J)

FIGS. 14A-14J depict vaginal sections stained with H&E of healthy control mice (14A-14B), of mice infected with *C. albicans* (14C-14D), of mice infected with *C. albicans* and treated with fluconazole (14E-14F), of mice infected with *C. albicans* and treated with dabigatran etexilate (14G-14H), and of mice infected with *C. albicans* and treated with both fluconazole and dabigatran etexilate (14I-14J) (10×=14A, 14C, 14E, 14G, 14I 40×=14B, 14D, 14F, 14H, 14J)

FIGS. 15A-15B depict photomicrographs (20×=15A, 40×=15B) of immunohistochemical staining of CD45 in control mice vaginal tissue. For IHC analysis, tissue sections were stained with anti-CD45 Ab and counterstained with hematoxylin. Stratified squamous epithelium (red star). Underlying lamina propria (blue star).

FIGS. 18A-18B depict photomicrographs (20×=18A, 40×=18B) of Immunohistochemical staining of CD45 in *C. albicans* infected and dabigatran etexilate treated mice vaginal tissue. CD4+ cells in infection foci were detected using anti-CD4 Ab by IHC. Examples of CD45-positive cell dye are indicated by black arrows; Notice that the number of CD4+ T cells was dramatically decreased after dabigatran etexilate treatment. Stratified squamous epithelium (red star). Underlying lamina propria (blue star).

FIGS. 19A-19B depict photomicrographs (20×=19A, 40×=19B) of Immunohistochemical staining of CD45 in *C. albicans* infected and fluconazole+dabigatran etexilate treated mice vaginal tissue. CD4+ cells in infection foci were detected using anti-CD4 Ab by IHC. Examples of CD45-positive cell dye are indicated by black arrows; Notice that the migration of CD4+ T cells was almost completely abolished after fluconazole compound 2 treatment. Stratified squamous epithelium (red star). Underlying lamina propria (blue star).

Similar reference characters denote corresponding features consistently throughout the attached drawings.

DETAILED DESCRIPTION OF THE PREFERRED EMBODIMENTS

Definitions

Figure 1:
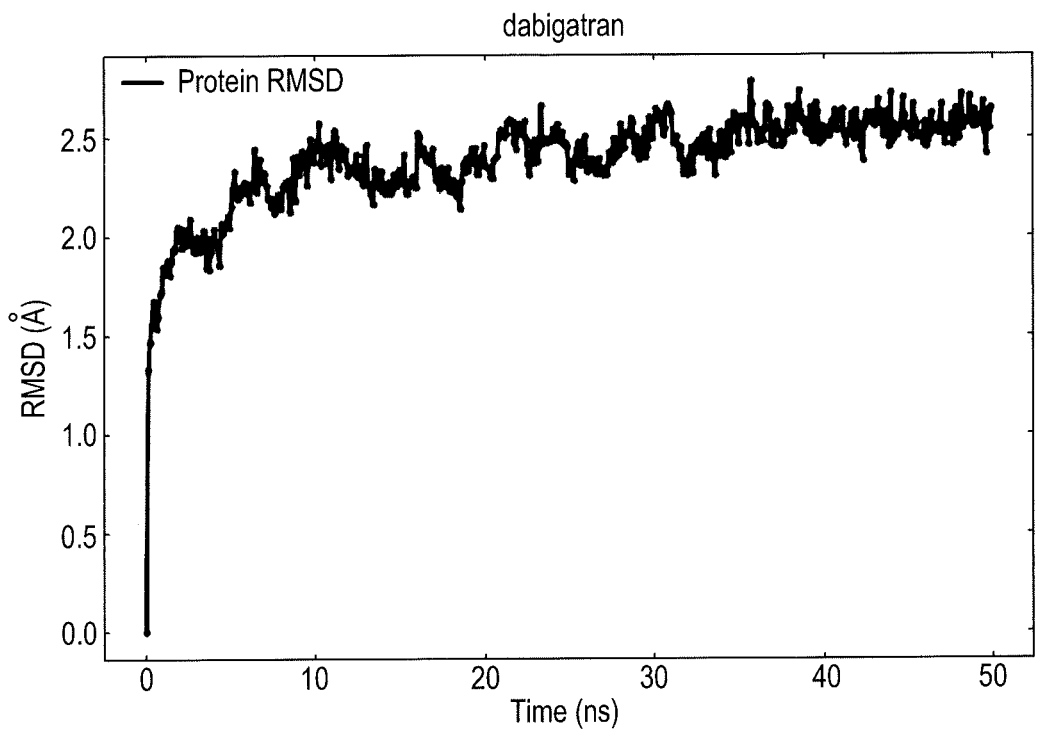
FIG. 1 depicts a graph of the RMSD of *C. albicans* 14-alpha demethylase bound with dabigatran.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

The phrase "pharmaceutically acceptable," as used herein, refers to molecular entities and compositions that do not produce an allergic or similar untoward reaction when administered to a human.

The term "subject," as used herein, means a mammal, including but not limited to a human being.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

As used herein, "dabigatran etexilate" refers to a prodrug having the chemical formula ($C_{34}H_{41}N_7O_5$). Dabigatran etexilate is commonly used as a blood thinner or anticoagulant to increase the blood fluidity in hematological and cardiovascular diseases e.g., stroke. Dabigatran etexilate is understood to reversibly bind to the active site of the thrombin molecule, thereby preventing thrombin-mediated activation of coagulation factors.

Treatment of Fungal Infections with Dabigatran Etexilate

A treatment of fungal infections using dabigatran etexilate can include administering a therapeutically effective amount of dabigatran etexilate ($C_{34}H_{41}N_7O_5$) to a subject in need thereof. In an embodiment, the dabigatran etexilate can be used to treat both topical and systemic infections. In an embodiment, the subject may be suffering from a fungal infection. In a further embodiment, the fungal infection may result from exposure to one or more of *Aspergillus flavus, Aspergillus fumigatus, Aspergillus nidulans, Aspergillus niger, Aspergillus terreus, Aspergillus ustus, Candida albicans, Candida alibicans, Candida glabrata, Candida lipolytica, Candida tropicalis, Candida tropicalis, Cryptococcus neoformans, Cryptococcus neoformas, Fusarium moniliforme, Geotricum candidum, Microsporum canis, Mucor circillelloides, Penicillium aurantiogriseum, Penicillium expansum, Penicillium italicum, Penicillium marneffei, Penicllium marneffeii, Rhizopus oryzaee, Sporotlirix schenckii, Syncephalastrum racemosum, Trichophyton mentagrophytes*, and *Trichophyton rubrum*.

As described herein, an investigation of FDA-approved drugs using virtual screening, bioinformatics, in vitro antifungal assays, in vivo mouse fungal infection models, and histopathological and immunohistochemical evaluation identified dabigatran etexilate as having broad-spectrum anti-fungal activity.

Using *Candida albicans* (*C. albicans*) 14-alpha demethylase (CYP51, 14AD) as a protein therapeutic target, a two-step virtual screening approach was used. First, the binding affinity of 1823 FDA-approved drugs was investigated. In a second run, the top 100 drugs were assessed using greater accuracy estimations of binding potency. Following an examination of virtual screening results, 18 medicines were chosen for in vitro anti-fungal testing. Among these, dabigatran etexilate demonstrated promising in vitro anti-fungal efficacy.

In vitro antifungal assays were performed for the 18 drugs on 31 fungal isolates. Dabigatran etexilate showed antifungal activity with MIC values in the range of 8-256 µg/ml, comprising *Aspergillus flavus* AUMC No. 1276, *Aspergillus flavus* RCMB 002002, *Aspergillus fumigatus* AUMC No. 14358, *Aspergillus fumigatus*(RCMB 002008), *Aspergillus nidulans* AUMC No. 14333, *Aspergillus niger* AUMC No. 14408, *Aspergillus niger* RCMB 002005, *Aspergillus terreus* AUMC No. 14389, *Aspergillus ustus* AUMC No. 3605, *Candida albicans* RCMB 005003 (1) ATCC 10231, *Candida alibicans* AUMC No. 9160, *Candida glabrata* AUMC No.

9166, *Candida lipolytica* RCMB 005007, *Candida tropicalis* AUMC No. 9158, *Candida tropicalis* RCMB 005004, *Cryptococcus neoformans* AUMC No. 2795, *Cryptococcus neoformas* RCMB 0049001, *Fusarium moniliforme* RCMB 001006, *Geotricum candidum* RCMB 026008, *Microsporum canis* AUMC No. 14454, *Mucor circillelloides* AUMC No. 3704, *Penicillium aurantiogriseum* IMI 89372, *Penicillium expansum* RCMB 001001 IMI28169, *Penicillium italicum* RCMB 001018 (1) IMI 193019, *Penicillium marneffei* AUMC No. 9370, *Penicillium marneffeii* RCMB 001034, *Rhizopus oryzaee* AUMC No. 14361, *Sporotlirix schenckii* AUMC No. 2739, *Syncephalastrum racemosum* RCMB 016001, *Trichophyton mentagrophytes* AUMC No. 14492 and *Trichophyton rubrum* AUMC No. 1804.

Three in vivo mouse anti-fungal models were used to elucidate the therapeutic effect of dabigatran etexilate on (1) *C. albicans* systemic infection, (2) *C. albicans* vaginal candidiasis, and (3) systemic *Aspergillus fumigatus* infection. Dabigatran etexilate either alone or in combination with fluconazole improved the health parameters, blood picture, liver, and kidney enzymes. In addition, the pathological changes in vaginal and internal organs were improved or completely alleviated by dabigatran etexilate treatment.

Accordingly, dabigatran etexilate has been demonstrated to be an effective broad-spectrum antifungal agent. A therapeutically effective amount of dabigatran etexilate or an amount effective to treat or prevent a fungal infection may be determined initially from the Examples described herein and adjusted for specific targeted diseases using routine methods.

In an embodiment, the dabigatran etexilate may be administered in a pharmaceutical composition further comprising a pharmaceutically acceptable carrier. In some embodiments, the pharmaceutical composition may be administered for oral administration. In these embodiments, the pharmaceutical composition may be used to treat a systemic or topical fungal infection.

The following examples illustrate the present teachings.

Example 1

Identifying Drug Candidates

Construction of Drugs and Compounds Dataset and Ligand Preparation

A set of FDA-approved drugs were retrieved. All compounds were loaded into Ligprep software, desalted, and 3D optimized at physiological pH using the OPLS2005 force field.

*Candida albicans* 14-Alpha Demethylase (CYP51, 14AD) Protein Preparation

The protein data bank was used to find the structure of CaCYP51 (PDB ID 5tz1). To process and optimize the protein structure, researchers employed the Maestro software package's protein preparation wizard (Schrodinger LLC, NY, USA). The protein was protonated to add polar hydrogens, the structure was optimized at cellular pH settings, and the structural energy was minimized with the OPLS2005 force field. All docking and molecular dynamics simulations in this investigation were performed using the generated structure.

Virtual Screening

All chemicals were docked using the Schrodinger glide docking module. Docking runs in two stages were completed. The compounds were docked using the conventional precision docking procedure at first (SP docking). Compounds with a docking score of −8.00 or higher were recovered and given further scrutiny (XP-docking). The docking grid was created by employing the co-crystallized ligand as the core of a docking box with a 20-size docking box. The obtained results were ranked based on the docking scores obtained.

Molecular Dynamics Simulations

The Groningen Machine for Chemical Simulations (GROMACS) 5.1.4 was used to perform molecular dynamics (MD) simulations. The ligand parameter, structure and constraint, and protein were generated using the AMBERFF14SB force field and the general AMBER force field (GAFF), respectively. The CaCYP51-ligand complexes were filled with a single point charge (SPC) water model and solvated in a cubic box of 1.0 nm from protein to box edge. For 5000 steps, the solvated CaCYP51-ligand complexes were reduced. The heavy atoms of protein and ligand were restricted during water and ions coupling. The entire system was equilibrated in two phases at 300K: 50 ps NVT (constant number of particles, volume, and temperature) ensemble, then 1 ns NPT (constant number of particles, pressure, and temperature) ensemble. The production steps were carried out with NPT ensemble over simulation durations of 20 and 100 ns. The Parrinello-Rahman algorithm keeps pressure constant at 1 bar, while the V-rescale thermostat method keeps temperature coupling at 300K. The Particle Mesh Ewald (PME) approach was used to restrict long-range electrostatics under periodic settings with a direct space cut-off of 12. The time step was set at 2 frames per second. Every 10 ps, coordinates and output data were collected. Tracking and analysis were carried out with the use of GROMACS MD simulation toolkits. For the root mean square deviation (RMSD) of the initial structure to the end of the simulation duration and the root mean square fluctuation (RMSF) of protein residues per residue, the g rms and g rmsf functions were employed. The g mmpbsa program was used to determine the binding free energy using Molecular mechanics-generalized Born surface area (MM-GBSA).

Docking and Virtual Screening Results

The present inventors have previously described methods of combined molecular modeling, virtual screening, and MD simulation to characterize biological aspects of microbial agents, illnesses, and drug discovery. (Altaher, Y. & Kandeel, M., "Molecular analysis of some camel cytochrome P450 enzymes reveals lower evolution and drug-binding properties", Journal of Biomolecular Structure and Dynamics, 34(1): pp. 115-24, (2016); Altaher, Y. et al., "Annotation of Camel Genome for Estimation of Drug Binding Power, Evolution and Adaption of Cytochrome P450", International Journal of Pharmacology, 11(3): pp. 243-7, (2015); Sheikh, A. et al., "Analysis of preferred codon usage in the coronavirus N genes and their implications for genome evolution and vaccine design," Journal of Virological Methods, 277: 113806 (2020).) An FDA-approved drug dataset was used for this investigation. The two-step process consisted of virtual screening and docking. Initial standard-precision (SP) docking protocols were carried out, with the compounds being selected for extra precision (XP) evaluation with a docking score of −8.00 or above (132 drugs) (Table 1). Within this set, dabigatran etexilate was raised as a potential antifungal agent after preliminary in vitro antifungal studies.

TABLE 1

Results of XP docking of FDA approved drugs against *C. albicans* 14-alpha demethylase

| Title | Molecular Weight | docking score | glide ligand efficiency | glide evdw | glide ecoul | glide energy |
|---|---|---|---|---|---|---|
| sennoside B | 862.7 | −20.2 | −0.3 | −56.9 | −23.1 | −80.0 |
| S4735 Salvianolic acid B | 718.6 | −18.8 | −0.4 | −66.1 | −40.1 | −106.2 |
| Glycyrrhizic acid | 822.9 | −17.6 | −0.3 | −66.7 | −21.0 | −87.7 |
| Ammonium Glycyrrhizinate | 840.0 | −17.4 | −0.3 | −68.6 | −19.0 | −87.6 |
| Neohesperidin dihydrochalcone | 612.6 | −17.0 | −0.4 | −49.5 | −23.0 | −72.5 |
| Diosmin | 608.5 | −16.6 | −0.4 | −42.6 | −20.7 | −63.3 |
| S3783 Echinacoside | 786.7 | −16.4 | −0.3 | −60.3 | −11.1 | −71.5 |
| S3923 Ginsenoside Rg1 | 801.0 | −16.4 | −0.3 | −40.9 | −18.3 | −59.3 |
| Naringin Dihydrochalcone | 582.6 | −16.1 | −0.4 | −50.1 | −18.9 | −69.0 |
| Naringin | 580.5 | −16.0 | −0.4 | −40.4 | −22.6 | −63.0 |
| Hesperidin | 610.6 | −15.9 | −0.4 | −55.6 | −16.6 | −72.2 |
| Neohesperidin | 610.6 | −15.6 | −0.4 | −57.0 | −17.6 | −74.6 |
| Rutin DAB10 | 610.5 | −15.5 | −0.4 | −47.8 | −23.8 | −71.6 |
| Atorvastatin calcium | 1155.3 | −14.4 | −0.4 | −57.2 | −10.9 | −68.1 |
| Acarbose | 645.6 | −14.3 | −0.3 | −49.3 | −19.4 | −68.7 |
| S3914 Hederin | 751.0 | −14.2 | −0.3 | −45.0 | −3.1 | −48.1 |
| Paclitaxel | 853.9 | −14.2 | −0.2 | −80.6 | −2.3 | −82.9 |
| S3743 Oxiglutatione | 612.6 | −14.1 | −0.4 | −61.4 | −27.1 | −88.5 |
| Docetaxel Trihydrate | 861.9 | −14.1 | −0.2 | −64.1 | −3.9 | −67.9 |
| Montelukast sodium | 608.2 | −14.1 | −0.3 | −59.8 | −11.6 | −71.4 |
| Lomitapide | 693.7 | −14.1 | −0.3 | −62.2 | −2.4 | −64.5 |
| Docetaxel | 807.9 | −13.9 | −0.2 | −65.4 | −3.5 | −68.9 |
| Oleuropein | 540.5 | −13.9 | −0.4 | −42.2 | −17.4 | −59.6 |
| Pirarubicin | 627.6 | −13.9 | −0.3 | −46.7 | −16.6 | −63.3 |
| S3668 Thymopentin | 679.8 | −13.9 | −0.3 | −59.6 | −24.5 | −84.2 |
| Digoxin | 780.9 | −13.9 | −0.3 | −75.1 | −5.1 | −80.2 |
| Polydatin | 390.4 | −13.8 | −0.5 | −29.8 | −23.0 | −52.9 |
| BMS-790052 | 738.9 | −13.8 | −0.3 | −62.7 | −6.6 | −69.3 |
| ABT-199 | 868.4 | −13.8 | −0.2 | −73.3 | −1.7 | −75.0 |
| S3612 Rosmarinic acid | 360.3 | −13.7 | −0.5 | −45.2 | −13.9 | −59.1 |
| LOPINAVIR (lopinavir) | 628.8 | −13.7 | −0.3 | −67.1 | −3.0 | −70.1 |
| Amygdalin | 457.4 | −13.6 | −0.4 | −39.9 | −14.8 | −54.7 |
| Lomitapide mesylate | 789.8 | −13.4 | −0.3 | −55.0 | −3.0 | −58.0 |
| Eltrombopag (Promacta) | 442.5 | −13.2 | −0.4 | −56.7 | −9.1 | −65.8 |
| Eltrombopag diethanolamine salt | 564.6 | −13.1 | −0.4 | −56.3 | −9.2 | −65.5 |
| S3925 (—)-Epicatechin gallate | 442.4 | −13.1 | −0.4 | −47.4 | −10.6 | −58.0 |
| Penfluridol | 524.0 | −13.1 | −0.4 | −53.8 | −3.6 | −57.4 |
| Silibinin | 482.4 | −12.9 | −0.4 | −54.7 | −4.9 | −59.5 |
| S3810 Scutellarin | 462.4 | −12.9 | −0.4 | −40.8 | −17.4 | −58.1 |
| S4896 Elagolix Sodium | 653.6 | −12.7 | −0.3 | −55.2 | −6.1 | −61.3 |
| S3901 Astragaloside IV | 785.0 | −12.7 | −0.2 | −4.1 | −11.5 | −15.6 |
| Empagliflozin (BI10773) | 450.9 | −12.7 | −0.4 | −40.2 | −10.5 | −50.7 |
| carfilzomib (PR-171) | 719.9 | −12.6 | −0.2 | −66.6 | −9.8 | −76.5 |
| Dabigatran etexilate | 627.7 | −12.6 | −0.3 | −68.6 | −10.1 | −78.7 |
| Mupirocin | 500.6 | −12.5 | −0.4 | −41.7 | −14.6 | −56.3 |
| S3714 Lifitegrast | 615.5 | −12.5 | −0.3 | −59.0 | −10.1 | −69.1 |
| Posaconazole | 700.8 | −12.5 | −0.2 | −67.2 | −2.8 | −70.1 |
| Dihydrostreptomycin sulfate | 1461.4 | −12.4 | −0.3 | −47.6 | −18.4 | −65.9 |
| NATACYN (natamycin) | 665.7 | −12.4 | −0.3 | −53.6 | −3.6 | −57.2 |
| Ellence (Epirubicin Hydrochloride) | 580.0 | −12.3 | −0.3 | −35.4 | −17.5 | −53.0 |
| AESCULIN | 340.3 | −12.3 | −0.5 | −27.9 | −17.2 | −45.1 |
| AP24534 | 532.6 | −12.2 | −0.3 | −55.2 | −8.6 | −63.8 |
| Novobiocin sodium | 634.6 | −12.2 | −0.3 | −54.2 | −9.7 | −63.9 |
| S4964 Lactobionic acid | 358.3 | −12.2 | −0.5 | −29.1 | −17.2 | −46.3 |
| Cobicistat (GS-9350) | 776.0 | −12.1 | −0.2 | −78.5 | −1.5 | −80.0 |
| Baicalin | 446.4 | −12.0 | −0.4 | −47.2 | −17.0 | −64.2 |
| Dapagliflozin (BMS-512148) | 408.9 | −12.0 | −0.4 | −39.0 | −10.3 | −49.4 |
| Amikacin sulfate | 781.8 | −12.0 | −0.3 | −48.9 | −9.5 | −58.4 |
| Aprepitant | 534.4 | −12.0 | −0.3 | −40.9 | −7.0 | −47.9 |
| Conivaptan hydrochloride | 535.0 | −12.0 | −0.3 | −56.6 | −0.9 | −57.4 |
| Itraconazole | 705.6 | −12.0 | −0.2 | −75.0 | 1.0 | −74.0 |
| Nelfinavir mesylate | 663.9 | −11.9 | −0.3 | −47.1 | −7.5 | −54.6 |
| Atazanavir Sulfate | 802.9 | −11.9 | −0.2 | −62.9 | −4.3 | −67.2 |
| cyclo (RGDfK) | 717.7 | −11.9 | −0.3 | −60.0 | −11.6 | −71.6 |
| Imidapril hydrochloride | 441.9 | −11.9 | −0.4 | −50.6 | −6.2 | −56.7 |
| ATP disodium salt | 551.1 | −11.9 | −0.4 | −45.1 | −26.8 | −71.8 |
| Atazanavir | 704.9 | −11.9 | −0.2 | −71.2 | −4.5 | −75.7 |
| S3824 Quercitrin | 448.4 | −11.8 | −0.4 | −38.4 | −14.1 | −52.5 |
| S3747 Levothyroxine sodium | 798.9 | −11.8 | −0.5 | −33.3 | −14.8 | −48.1 |
| Canagliflozin | 444.5 | −11.8 | −0.4 | −43.6 | −7.0 | −50.6 |

TABLE 1-continued

Results of XP docking of FDA approved drugs against *C. albicans* 14-alpha demethylase

| Title | Molecular Weight | docking score | glide ligand efficiency | glide evdw | glide ecoul | glide energy |
|---|---|---|---|---|---|---|
| Fulvestrant | 606.8 | −11.8 | −0.3 | −48.4 | −5.6 | −54.0 |
| Clindamycin hydrochloride | 699.9 | −11.7 | −0.3 | −59.4 | −3.3 | −62.8 |
| Pranlukast | 481.5 | −11.7 | −0.3 | −54.0 | −5.9 | −59.9 |
| Azelnidipine | 582.6 | −11.7 | −0.3 | −67.9 | −3.2 | −71.2 |
| Nebivolol HCl (R-067555) | 441.9 | −11.7 | −0.4 | −37.4 | −10.6 | −48.0 |
| Imatinib Mesylate | 589.7 | −11.7 | −0.3 | −57.6 | −5.1 | −62.8 |
| S5013 Ioversol | 807.1 | −11.6 | −0.4 | −42.7 | −16.3 | −59.0 |
| S4977 Efonidipine | 631.7 | −11.6 | −0.3 | −56.0 | −6.5 | −62.6 |
| BAF312 (Siponimod) | 516.6 | −11.6 | −0.3 | −45.8 | −10.0 | −55.8 |
| NADIDE | 663.4 | −11.6 | −0.3 | −62.5 | −15.6 | −78.1 |
| Cabazitaxel | 835.9 | −11.6 | −0.2 | −60.7 | −5.3 | −66.0 |
| Chlorhexidine Hydrochloride | 578.4 | −11.5 | −0.3 | −58.9 | −5.6 | −64.4 |
| Quinapril hydrochloride | 475.0 | −11.4 | −0.4 | −52.8 | −4.6 | −57.5 |
| Imatinib | 493.6 | −11.4 | −0.3 | −58.3 | −4.5 | −62.8 |
| Paeoniflorin | 480.5 | −11.4 | −0.3 | −41.2 | −12.4 | −53.6 |
| S3930 Liquiritin | 418.4 | −11.4 | −0.4 | −43.1 | −5.6 | −48.7 |
| Sofosbuvir (PSI-7977) | 529.5 | −11.4 | −0.3 | −55.9 | −8.0 | −63.9 |
| S3842 Isoquercitrin | 464.4 | −11.4 | −0.3 | −38.7 | −18.3 | −57.0 |
| Labetalol hydrochloride | 364.9 | −11.4 | −0.5 | −40.9 | −9.9 | −50.8 |
| CARVEDILOL (carvedilol) | 406.5 | −11.4 | −0.4 | −46.6 | −4.0 | −50.6 |
| ATACAND (candesartan cilexetil) | 610.7 | −11.3 | −0.3 | −61.7 | −5.7 | −67.3 |
| S4597 Lercanidipine (hydrochloride) | 648.2 | −11.3 | −0.3 | −50.7 | −1.3 | −52.0 |
| Fexofenadine HCl | 538.1 | −11.3 | −0.3 | −40.5 | −9.3 | −49.8 |
| TIKOSYN (dofetilide) | 441.6 | −11.3 | −0.4 | −49.3 | −9.4 | −58.8 |
| S3957 Gamma-Oryzanol | 602.9 | −11.3 | −0.3 | −49.4 | 0.7 | −48.7 |
| AV-951 | 454.9 | −11.2 | −0.4 | −55.1 | −5.3 | −60.4 |
| Salmeterol xinafoate | 603.7 | −11.2 | −0.4 | −47.2 | −3.7 | −50.9 |
| Curcumin | 368.4 | −11.2 | −0.4 | −36.8 | −7.8 | −44.6 |
| ODM-201 | 398.8 | −11.1 | −0.4 | −50.0 | −9.2 | −59.3 |
| Lapatinib freebase | 581.1 | −11.1 | −0.3 | −66.8 | −5.1 | −71.9 |
| Silymarin | 482.4 | −11.1 | −0.3 | −47.8 | −5.5 | −53.3 |
| IPI-145 | 416.9 | −11.0 | −0.4 | −52.2 | −7.3 | −59.5 |
| EXJADE (deferasirox) | 373.4 | −11.0 | −0.4 | −42.4 | −11.5 | −53.9 |
| Linezolid | 477.5 | −11.0 | −0.3 | −57.2 | −11.0 | −68.2 |
| Clinofbrate | 468.6 | −11.0 | −0.3 | −40.9 | −13.0 | −53.9 |
| VUMON (teniposide) | 656.7 | −11.0 | −0.2 | −43.0 | −7.4 | −50.4 |
| ENALAPRILAT (enalaprilat) | 384.4 | −10.9 | −0.4 | −47.8 | −7.9 | −55.7 |
| Kanamycin sulfate | 582.6 | −10.9 | −0.3 | −35.6 | −13.9 | −49.5 |
| LIQUID PRED (Lisinopril) | 405.5 | −10.9 | −0.4 | −44.2 | −6.7 | −50.9 |
| S3727 Vilanterol Trifenate | 774.8 | −10.8 | −0.3 | −47.3 | −7.6 | −54.9 |
| RAPAFLO (silodosin) | 495.5 | −10.8 | −0.3 | −47.7 | −2.5 | −50.2 |
| Chlorogenic acid | 354.3 | −10.7 | −0.4 | −28.0 | −15.1 | −43.1 |
| S3664 Flupenthixol dihydrochloride | 507.4 | −10.7 | −0.4 | −27.1 | −5.7 | −32.8 |
| Adriamycin (Doxorubicin Hydrochloride) | 580.0 | −10.6 | −0.3 | −42.7 | −13.5 | −56.2 |
| R 788 | 624.4 | −10.6 | −0.3 | −51.1 | −8.9 | −60.0 |
| Neomycin sulfate | 712.7 | −10.5 | −0.3 | −46.3 | −11.1 | −57.3 |
| S3645 Kitasamycin | 786.0 | −10.5 | −0.2 | −52.2 | −0.4 | −52.5 |
| Puerarin | 432.4 | −10.5 | −0.3 | −45.9 | −10.1 | −56.0 |
| Terfenadine | 471.7 | −10.4 | −0.3 | −46.0 | −2.5 | −48.4 |
| TELAPREVIR (VX-950) | 679.8 | −10.2 | −0.2 | −58.8 | −3.1 | −61.9 |
| S4610 Mebendazole | 295.3 | −10.2 | −0.5 | −35.1 | −6.5 | −41.6 |
| Loperamide HCl | 513.5 | −10.2 | −0.3 | −38.6 | −4.2 | −42.8 |
| Domperidone | 425.9 | −10.1 | −0.3 | −48.5 | −2.1 | −50.5 |
| Ticagrelor | 522.6 | −10.1 | −0.3 | −45.1 | −9.5 | −54.6 |
| Aliskiren hemifumarate | 1219.6 | −10.1 | −0.3 | −52.0 | −5.2 | −57.1 |
| Amikacin hydrate | 603.6 | −9.9 | −0.2 | −44.3 | −8.4 | −52.8 |
| Dronedarone hydrochloride | 593.2 | −9.8 | −0.3 | −57.2 | −5.8 | −63.0 |
| S3670 Cefsulodin (sodium) | 554.5 | −9.5 | −0.3 | −50.3 | −10.5 | −60.8 |
| S5012 Octenidine Dihydrochloride | 623.8 | −9.4 | −0.2 | −59.7 | 0.3 | −59.4 |
| Ritonavir | 720.9 | −8.1 | −0.2 | −55.8 | −6.5 | −62.3 |

Molecular Dynamics Simulations

Figure 2:
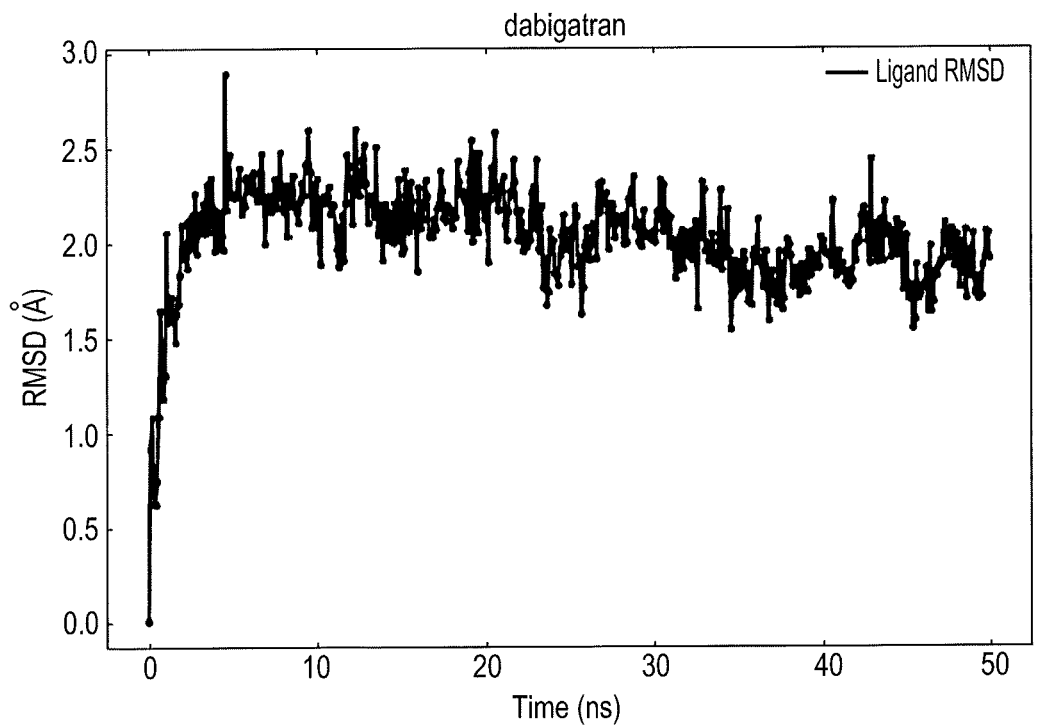
FIG. 2 depicts a graph of the ligand RMSD of dabigatran bound with *C. albicans* 14-alpha demethylase.

Docking with MD simulation is a powerful drug discovery approach. Based on binding affinity, binding energy, and drug-receptor dynamics, compounds can be rated. After 50 ns MDs, the average protein RMSD value was 2.4 Å (FIG. 1). The ligand RMSD of dabigatran etexilate (FIG. 2) showed lower RMSD values compared with the protein RMSD, indicating a stable binding pattern during the simulation. Visual as well as calculated parameters supported the stable binding of dabigatran etexilate with C. albicans 14-alpha demethylase (data not shown).

Figure 3:
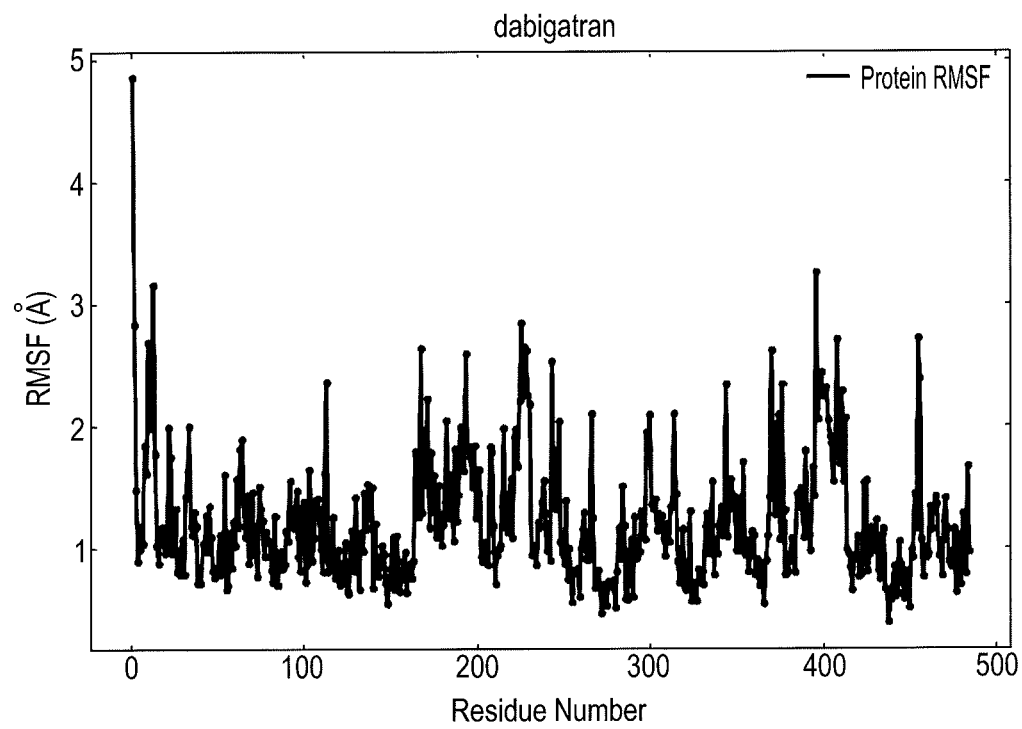
FIG. 3 depicts a graph of the RMSF of *C. albicans* 14-alpha demethylase bound with dabigatran etexilate for 50 ns.

An RMSF plot (FIG. 3) indicated fixation of C. albicans 14-alpha demethylase active site residues and lower fluctuation of all of the protein indicating the power of dabigatran etexilate binding.

Figure 4:
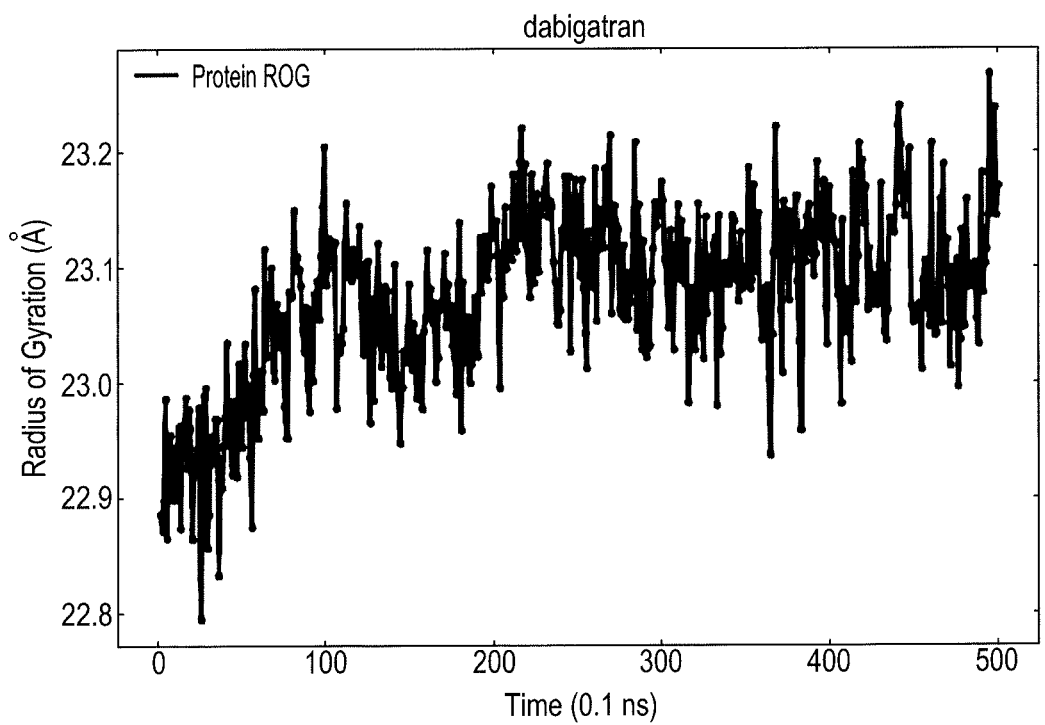
FIG. 4 depicts a graph of the variation in Rg obtained during 50 ns MD simulations *C. albicans* 14-alpha demethylase bound with dabigatran etexilate.

The radius of gyration (Rg) can be used to determine the compactness of a system, with higher Rg values suggesting lower compactness or more unfolded protein, and lower Rg values indicating more stable structures. Dabigatran etexilate had an average Rg value of 2.31 nm: indicating the stability of the drug. FIG. 4 shows the variation in Rg obtained during 50 ns MD simulations.

Example 2

In Vitro Antifungal Assays

In vitro studies were performed including a total of 31 fungal strains. The strains were obtained from the American Type Culture Collection (ATCC) or were isolated locally and provided by the fungal research centers at Alazhar and Assiut universities, Egypt. Dabigatran's antifungal activity was tested against 31 fungal strains, as previously described. (Johnson, T. R. and Case, C. L., "Laboratory experiments in microbiology" Pearson/Benjamin Cummings (2004)) The in vitro studies included a total of 31 fungal strains. Fungal strains were separately grown in universal tubes with 20 ml of Sabouraud's dextrose broth for 3-7 days to create inocula for antifungal tests. Bioassays were carried out in 10 cm sterile Petri dishes containing 15 ml Sabouraud's dextrose agar medium and microbial suspension. Using a sterile cork borer, 5 mm diameter cavities were bored in the solidified agar (3 cavities/plate) after the media had hardened. Dabigatran etexilate was dissolved in DMSO, serially diluted (0.001-1 mg/ml) and 50 µl of it was put to the plate's hollow. Controls were prepared using DMSO and fluconazole. Candida cultures were incubated for 72 hours at 27° C., while other fungal cultures were incubated for up to seven days.

Dabigatran etexilate showed antifungal activity on thirty fungal strains in vitro (Table 2). The range of obtained MIC values was 8-256 µg/ml.

TABLE 2

MIC Values of Dabigatran Etexilate Against 31 Fungal Strains

| Fungal strains | MIC (µg/ml) |
|---|---|
| Aspergillus flavus AUMC No. 1276 | 64 |
| Aspergillus flavus RCMB 002002 | 128 |
| Aspergillus fumigatus AUMC No. 14358 | 128 |
| Aspergillus fumigatus (RCMB 002008) | 64 |
| Aspergillus nidulans AUMC No. 14333 | 64 |
| Aspergillus niger AUMC No. 14408 | 128 |
| Aspergillus niger RCMB 002005 | 0 |
| Aspergillus terreus AUMC No. 14389 | 128 |
| Aspergillus ustus AUMC No. 3605 | 64 |
| Candida albicans RCMB 005003 (1) ATCC 10231 | 16 |
| Candida alibicans AUMC No. 9160 | 32 |
| Candida glabrata AUMC No. 9166 | 32 |
| Candida lipolytica RCMB 005007 | 16 |
| Candida tropicalis AUMC No. 9158 | 128 |
| Candida tropicalis RCMB 005004 | 128 |
| Cryptococcus neoformans AUMC No. 2795 | 32 |
| Cryptococcus neoformas RCMB 0049001 | 16 |
| Fusarium moniliforme RCMB 001006 | 16 |
| Geotricurn candidum RCMB 026008 | 32 |
| Microsporum canis AUMC No. 14454 | 128 |
| Mucor circillelloides AUMC No. 3704 | 64 |
| Penicillium aurantiogriseum IMI 89372 | 32 |
| Penicillium expansurn RCMB 001001 IMI28169 | 128 |
| Penicillium italicum RCMB 001018 (1) IMI 193019 | 64 |
| Penicillium marneffei AUMC No. 9370 | 64 |
| Penicllium marneffeii RCMB 001034 | 256 |
| Rhizopus oryzaee AUMC No. 14361 | 0 |
| Sporotlirix schenckii AUMC No. 2739 | 16 |
| Syncephalastrurn racemosum RCMB 016001 | 8 |
| Trichophyton mentagrophytes AUMC No. 14492 | 32 |
| Trichophyton rubrum AUMC No. 1804 | 32 |

Example 3

In Vivo Systemic Antifungal Assays

Animals

Four-week-old mice were obtained from Kafrelshikh university animal sourcing. Food and water were given ad libitum. The mice were handled according to the instructions and regulations of the ethics committee.

Systemic Fungal Infection (Systemic Aspergillus and Candida Infection)

To help in the induction of fungal infection, mice were immunocompromised by Endoxan® (cyclophosphamide), injected i.v. at a dose rate of 100 mg/kg. The injection of cyclophosphamide was at three and one days before infection. Systemic candidiasis and aspergillosis were induced by intravenous injection of 0.2 ml of each cell suspension into the tail vein using 1-ml syringe and a 27-G, ½-in. needle. The C. albicans cells and Aspergillus conidia were obtained as described above. After plating, the cells were suspended in sterile saline. Each mouse received $5 \times 10^4$ blastospores. All drugs were given at a dose rate of 5 mg/kg via the oral route suspended in methylcellulose. Five groups of eight mice were allocated as follows 1—non-infected non-treated control group, 2—injected with Candida or Aspergillus without treatment, 3—injected with Candida or Aspergillus and treated with fluconazole, 4—injected with Candida or Aspergillus and treated with dabigatran etexilate, and 5—injected with Candida or Aspergillus and treated with fluconazole+dabigatran etexilate combination. Treatment was continued daily for seven days. On the seventh day, the mice were sacrificed, and blood and tissue samples were collected. Tissue samples from liver, kidney, lungs, and heart were stored in 10% formalin and fixed for histopathological and immunohistochemical examination.

Histopathological and Immunohistochemical Exam

Standard histopathological sections stained with hematoxylin and eosin were performed. Immunohistochemistry was performed following the instructions of the antibodies manufacturer (Theiino Scientific, Waltman, MA, USA). The antibodies comprised CD45 and CXCR4.

Histopathological Evaluation of Systemic Candidiasis: Liver

Figure 5A:
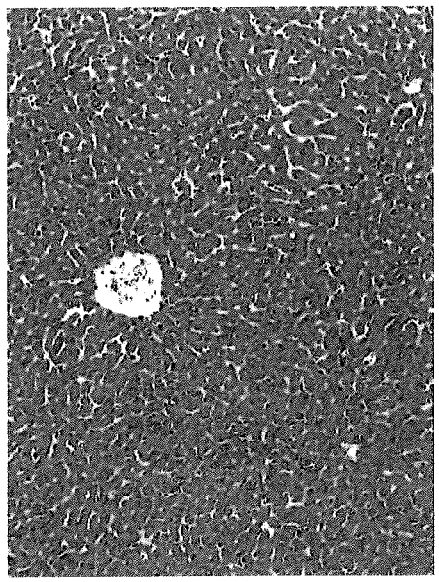
FIGS. 5A-5J depict histopathological examination of liver sections of healthy control mice (5A-5B), of mice infected with *C. albicans* (5C-5D), of mice infected with *C. albicans* and treated with fluconazole (5E-5F), of mice infected with *C. albicans* and treated with dabigatran etexilate (5G-5H), and of mice infected with *C. albicans* and treated with both fluconazole and dabigatran etexilate (5I-5J). (10×=5A, 5C, 5E, 5G, 5I 40×=5B, 5D, 5F, 5H, 5J)
Figure 5B:
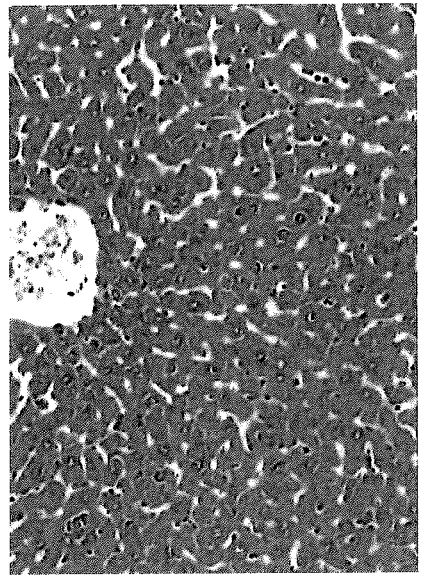
Figure 5C:
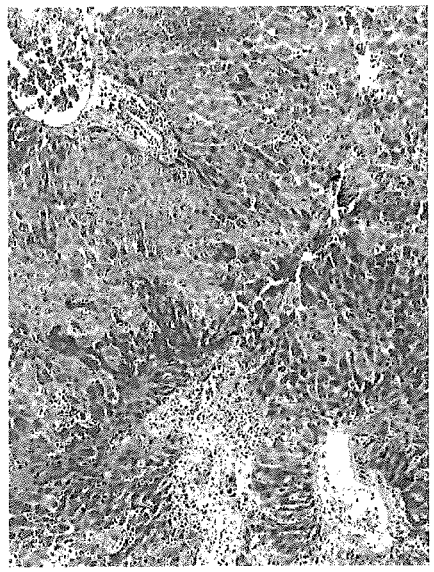
Figure 5D:
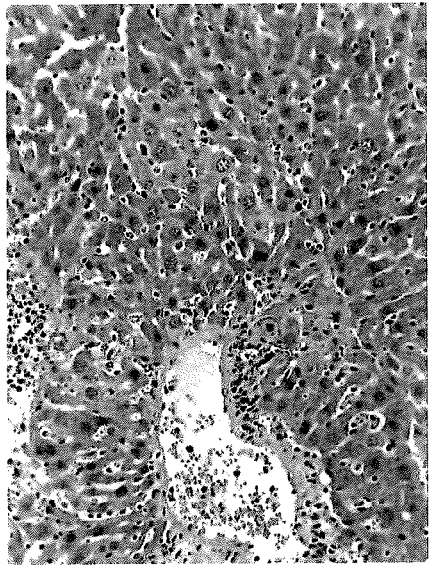
Figure 5E:
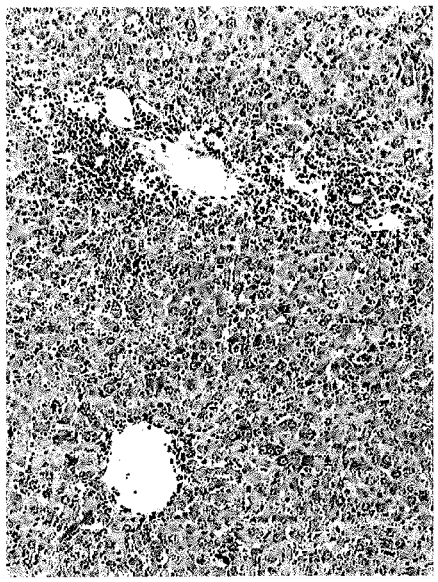
Figure 5F:
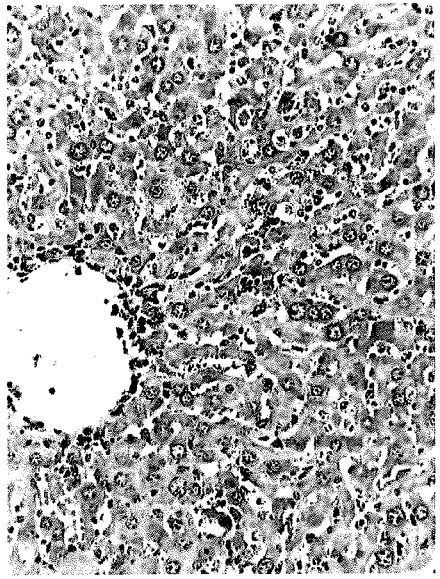
Figure 5G:
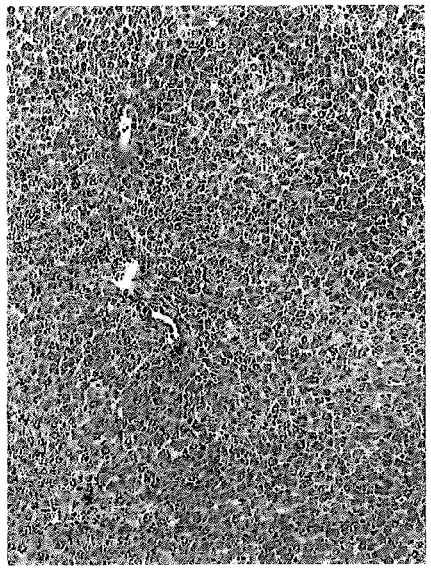
Figure 5H:
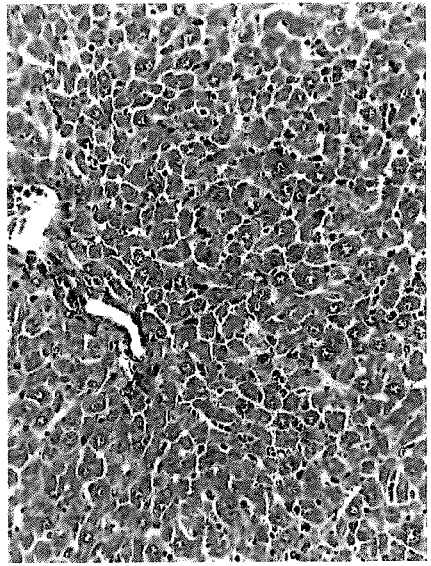
Figure 5I:
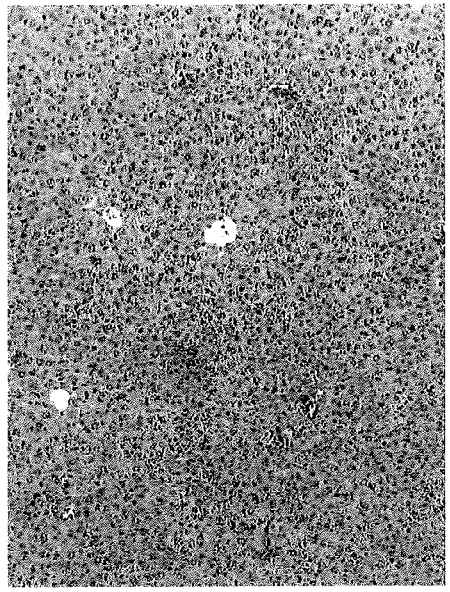
Figure 5J:
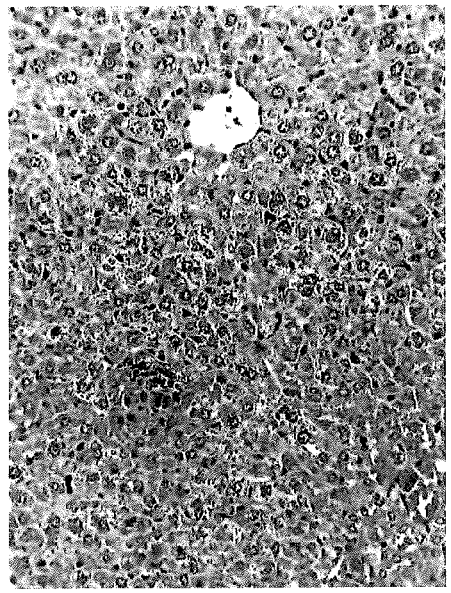

The histological analysis of liver sections of the control animals showed typical liver structure with rows of polyhedral hepatocytes, well-preserved cytoplasm, and prominent nucleus without any signs of vascular or inflammatory changes (See FIGS. 5A and 5B). The liver sections of *C. albicans* infected animals showed evident changes of acute hepatocellular injury. These anomalies included intense vascular and sinusoidal hyperemia, aggregation of inflammatory cells, degenerated hepatocytes, and apoptotic cells as well as cell necrosis (See FIGS. 5C and 5D). Apoptosis morphology, as chromatin condensation or margination of shrunk hepatocytes, could be seen. The liver sections of mice infected with *C. albicans* and treated with fluconazole showed moderate inflammatory cell infiltration in the perivascular regions, mild sinusoidal congestion, and few apoptotic cells (See FIGS. 5E and 5F). The sections of liver taken from the animals infected with *C. albicans* and treated with fluconazole and or dabigatran etexilate showed the typical hepatic architecture with the presence of very few inflammatory cells, moderate degeneration, and no necrosis (See FIGS. 5G-5J).

Histopathological Evaluation of Systemic Candidiasis: Heart

Figure 6A:
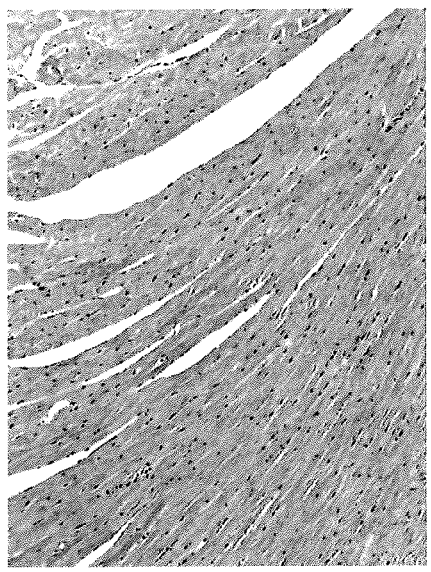
FIGS. 6A-6J depict histopathological examination of heart sections of healthy control mice (6A-6B), of mice infected with *C. albicans* (6C-6D), of mice infected with *C. albicans* and treated with fluconazole (6E-6F), of mice infected with *C. albicans* and treated with dabigatran etexilate (6G-6H), and of mice infected with *C. albicans* and treated with both fluconazole and dabigatran etexilate (6I-6J). (10×=6A, 6C, 6E, 6G, 6I 40×=6B, 6D, 6F, 6H, 6J)
Figure 6B:
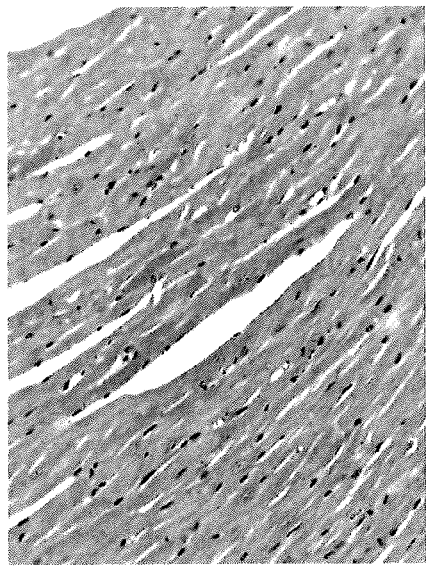
Figure 6C:
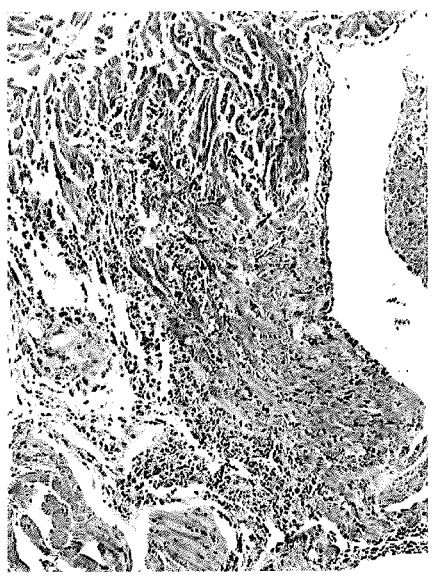
Figure 6D:
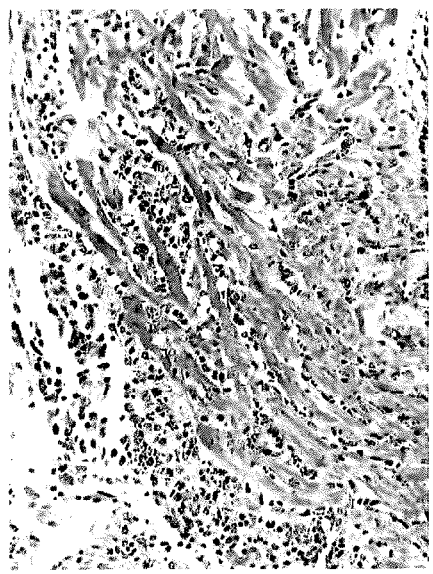
Figure 6E:
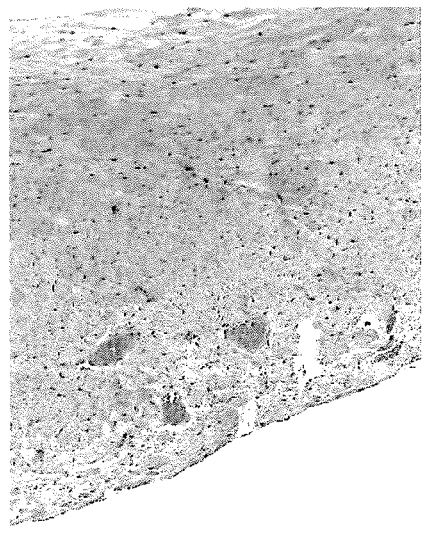
Figure 6F:
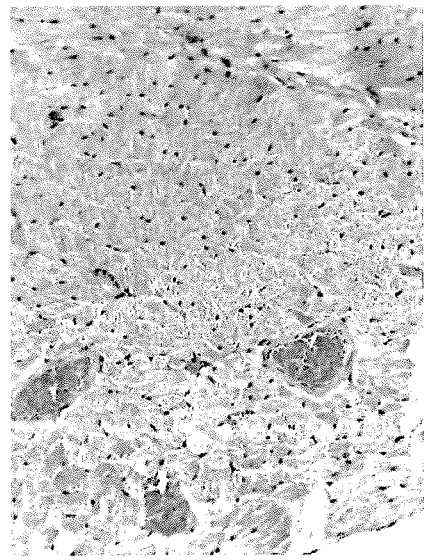
Figure 6G:
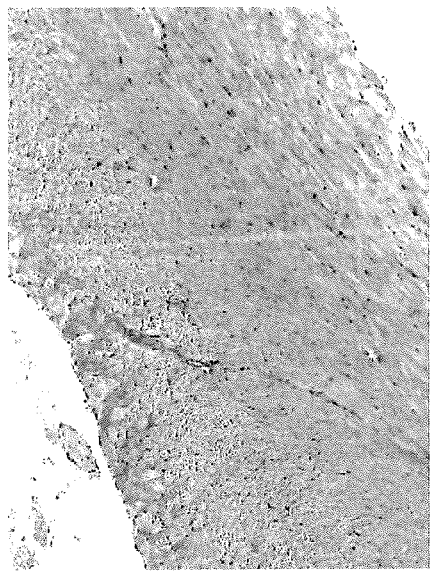
Figure 6H:
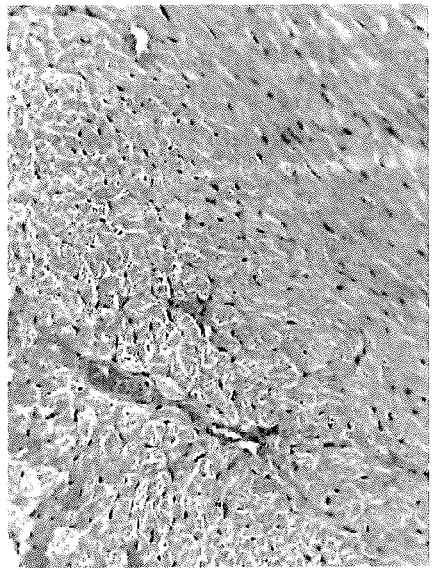
Figure 6I:
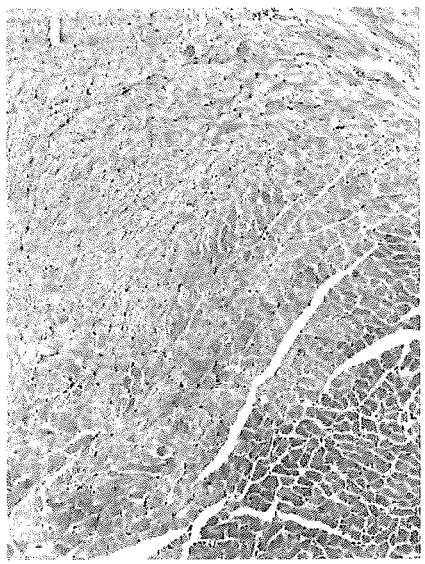
Figure 6J:
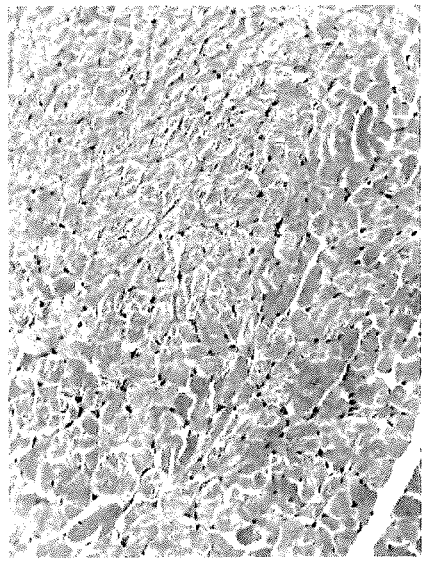

Histological examinations of heart tissues of the control group demonstrated typical myocardial fiber architecture and branched muscle fibers with central oval nuclei. (See FIGS. 6A and 6B) When the myocardial tissues from the *C. albicans*-infected group were compared with those from the non-infected control group, considerable pathological changes have been observed in the myocardial tissues in the *C. albicans*-infected group. The changes observed in the *C. albicans*-infected group involved loss of the typical muscle fiber architecture, loss of cross striations, fragmentation of sarcoplasm, a few scattered foci of lymphocytic infiltration with smaller numbers of macrophages consistent with myocyte degeneration or even necrosis (See FIGS. 6C and 6D). However, in the treated groups, the histologic findings were significantly improved compared with non-treated *C. albicans*-infected mice, although there was a mild histologic change in the myocardial tissues in the treated groups in the form of degenerative changes in myocardial fibers with congested blood vessels (See FIGS. 6E-6J). Furthermore, no inflammatory reaction could be identified.

Histopathological Evaluation of Systemic Candidiasis: Lung

Figure 7A:
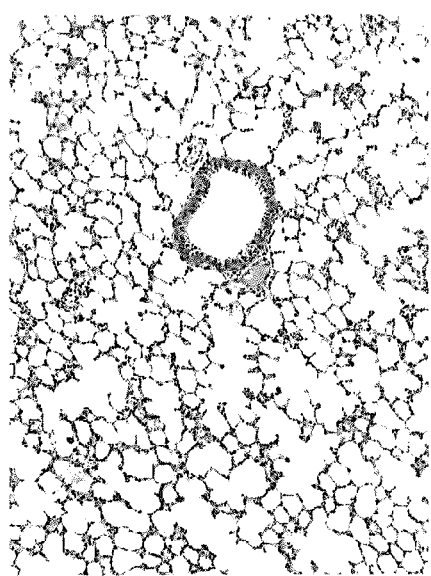
Figure 7B:
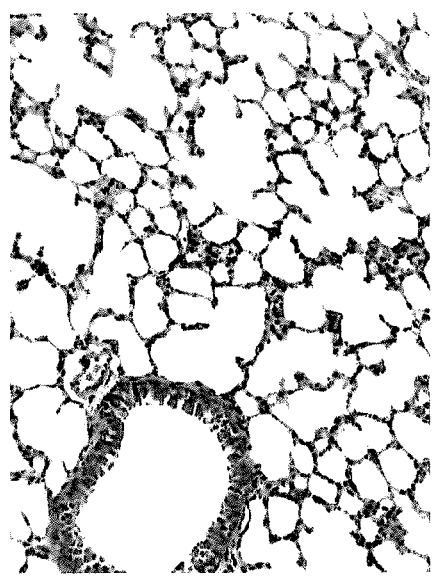
Figure 7C:
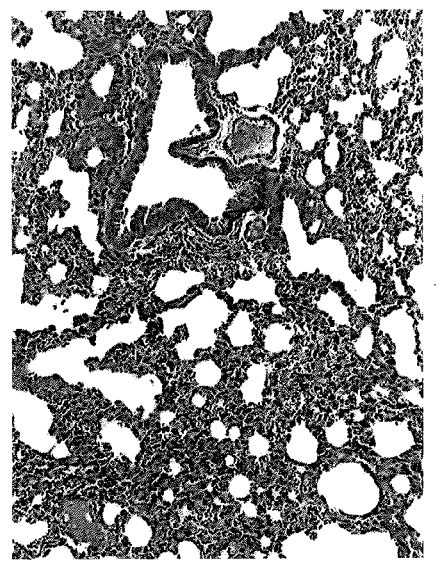
Figure 7D:
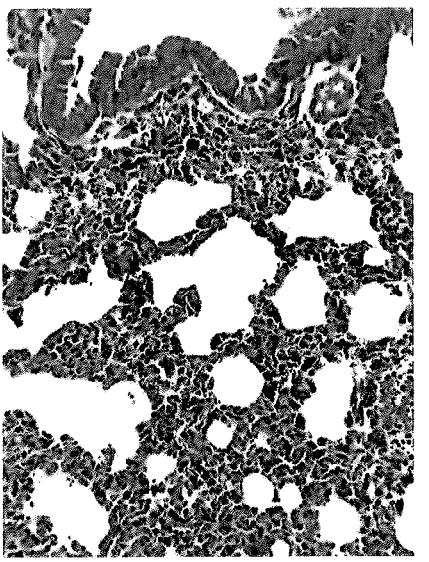
Figure 7I:
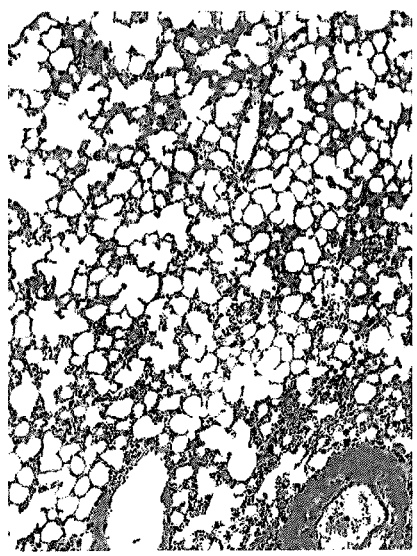
Figure 7J:
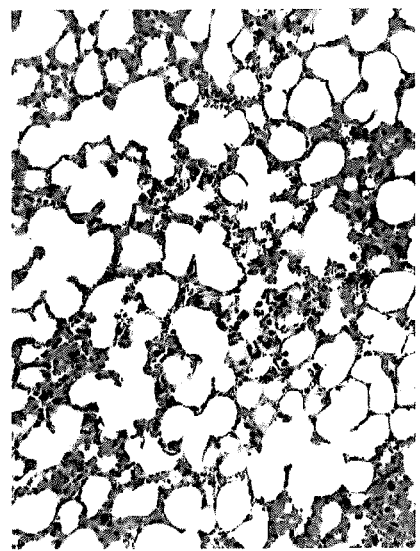

Histological investigations were performed in H&E-stained lung tissues. Control rats' lungs showed normal spongy histological structure and the alveoli appeared patent with thin interalveolar septa with no inflammatory cell infiltration or discernible damage (See FIGS. 7A and 7B). By comparison, lung sections of mice infected with *C. albicans* were disturbed with thickened alveolar wall and decreased airspace areas because of red blood cells extravasation and the infiltration of a considerable number of inflammatory cells (See FIGS. 7C and 7D). Treatment with fluconazole slightly ameliorated the lung damage induced by *C. albicans* as shown by a mild decrease in infiltration of inflammatory cells and reduced thickness of alveolar septa compared with *C. albicans*-infected animals (See FIGS. 7E and 7F). However, in the group injected with *Candida* and treated with dabigatran etexilate or fluconazole+dabigatran etexilate, the histologic findings were substantially improved when compared with non-treated *C. albicans* infected mice, although there were mild histological alterations in the lung tissues of both groups and infiltration of few inflammatory cells in the lung, and the red blood cells extravasation was also dramatically improved (See FIGS. 7G-7J).

Histopathological Evaluation of Systemic Candidiasis: Kidney

Figure 8A:
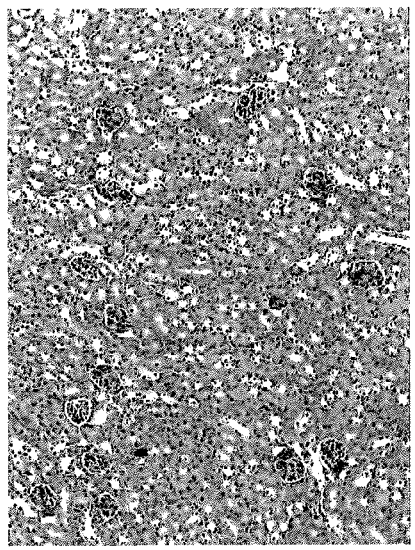
FIGS. 8A-8J depict histopathological examination of kidney sections of healthy control mice (8A-8B), of mice infected with *C. albicans* (8C-8D), of mice infected with *C. albicans* and treated with fluconazole (8E-8F), of mice infected with *C. albicans* and treated with dabigatran etexilate (8G-8H), and of mice infected with *C. albicans* and treated with both fluconazole and dabigatran etexilate (8I-8J). (10×=8A, 8C, 8E, 8G, 8I 40×=8B, 8D, 8F, 8H, 8J)
Figure 8B:
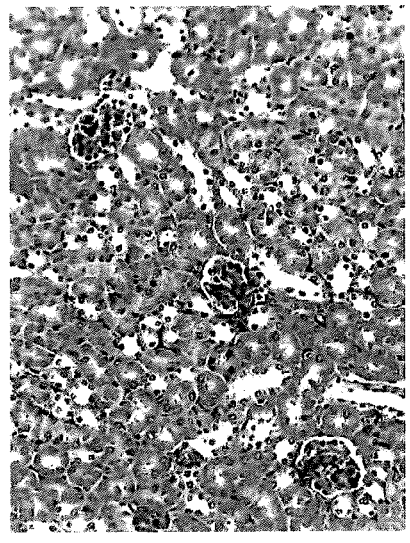
Figure 8C:
Figure 8D:
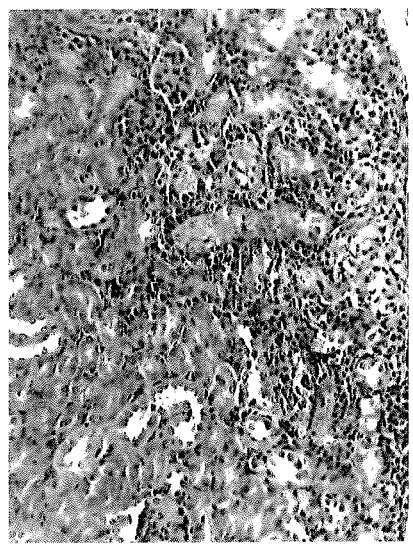
Figure 8E:
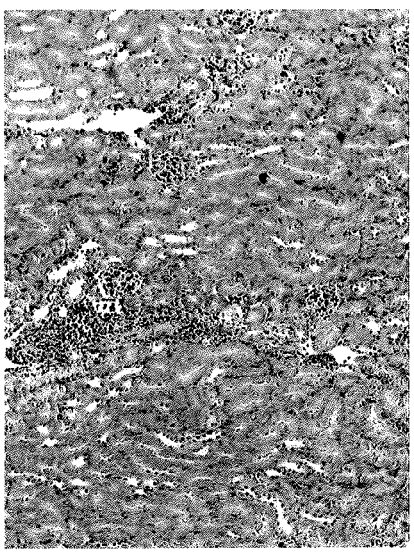
Figure 8F:
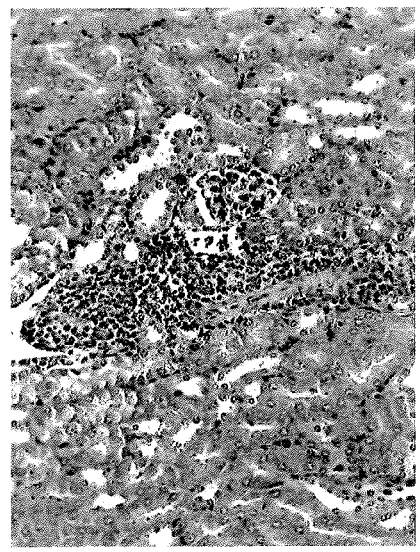
Figure 8G:
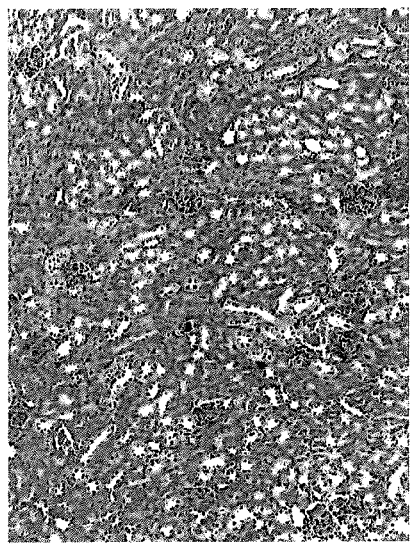
Figure 8H:
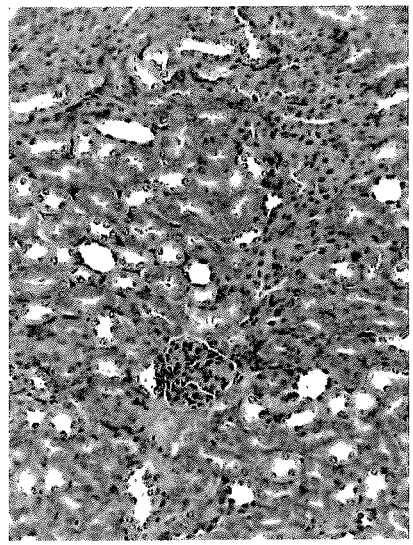
Figure 8I:
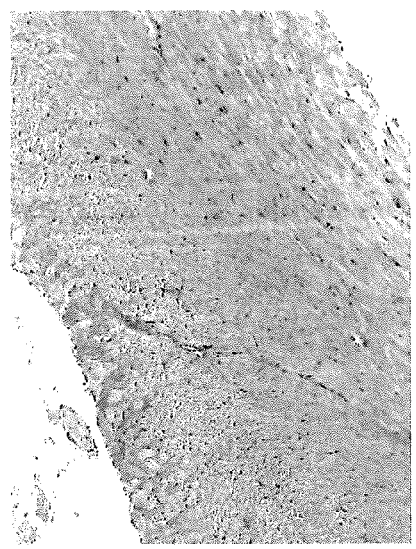
Figure 8J:
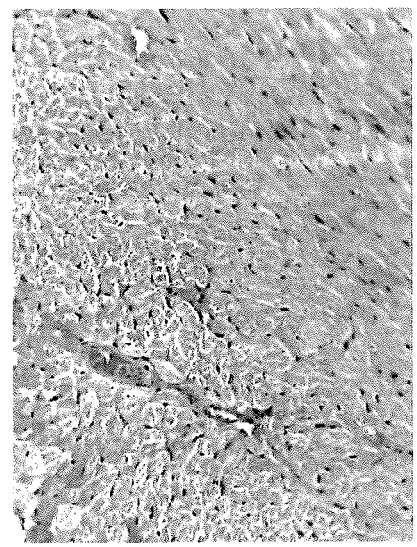

The kidneys of the control mice had typical cortical and medulla histology with normal glomeruli, tubules, and vessels but with no evidence of cell necrosis or inflammatory infiltration (See FIGS. 8A and 8B). However, dramatic injury was evident in *C. albicans* infected animals. The kidneys showed infiltration of inflammatory cells in the cortical and medullary regions. Numerous proximal convoluted tubules had necrotic and detached epithelial cells, some of which had been denuded entirely (See FIGS. 8C and 8D). Similar histological alterations were also observed in animals treated with fluconazole (See FIGS. 8E and 8F). Moreover, it was possible to notice that the glomeruli in these groups displayed structural alterations such as diminished glomeruli size, reduced Bowman's spaces, and increased cellularity compared with those in the control group. However, minor histological differences were observed in animals infected with *C. albicans* and treated with dabigatran etexilate and fluconazole+dabigatran etexilate groups with restricted renal injury, reduced hyperemia, and conserved glomerulus architecture (See FIGS. 8G-8J). These findings indicate that dabigatran etexilate has a potent protective effect against systemic *C. albicans* fungal infection in mice.

Histopathological Evaluation of Systemic Aspergillosis: Liver

Figure 9A:
Figure 9B:
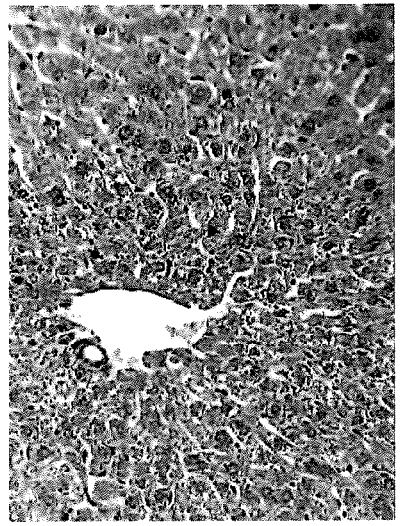
Figure 9C:
Figure 9D:
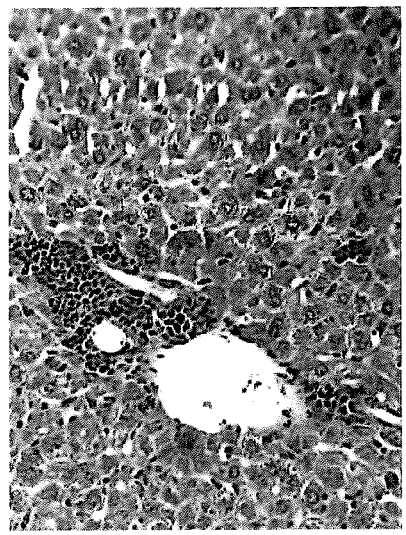
Figure 9E:
Figure 9F:
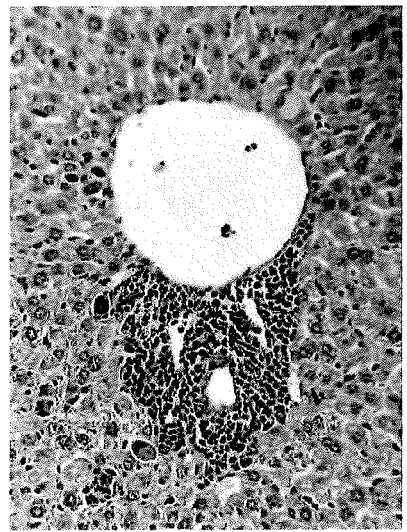
Figure 9G:
Figure 9H:
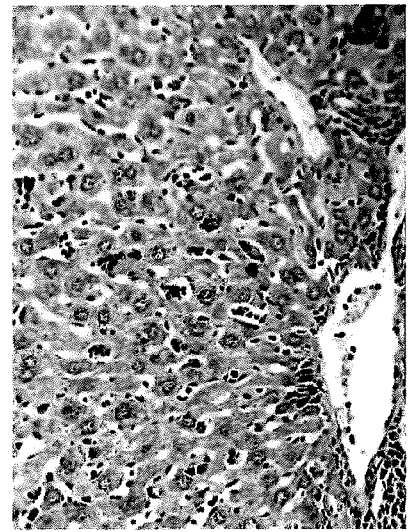

The typical arrangement of hepatocytes around the central vein was observed in microscopic liver sections from mice in the control group, and there were no indications of necrosis or inflammation (See FIGS. 9A and 9B). Hepatocellular damage was evident in the liver parts of *A. fumigatus*-infected animals. Mononuclear cell infiltration in and around congested blood vessels, as well as hydropic degeneration, and mitotic figures in the hepatic parenchyma, were among the alterations discovered (See FIGS. 9C and 9D). Comparable histopathological injuries were seen in mice infected with *A. fumigatus* and treated with fluconazole and dabigatran. Increased number of Kupffer cells, as well as hepatocyte's apoptosis with hyper eosinophilic cytoplasm and densely stained nucleus, pyknotic and less vacuolation, was noticed in these groups (See FIGS. 9E-9J). The nuclei of some hepatocytes were pale or absent. Some hepatocytes were hypertrophic. Binucleated hepatic cells were also noted.

Histopathological Evaluation of Systemic Aspergillosis: Heart

Figure 10C:
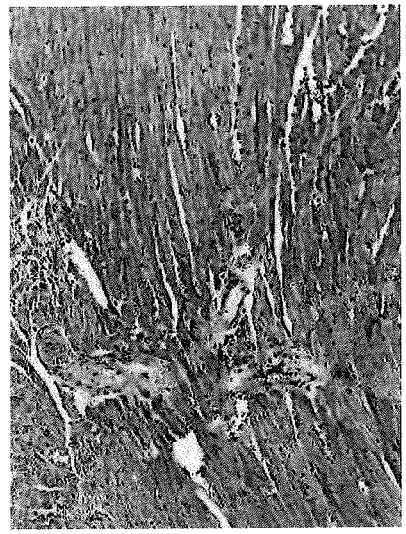
Figure 10D:
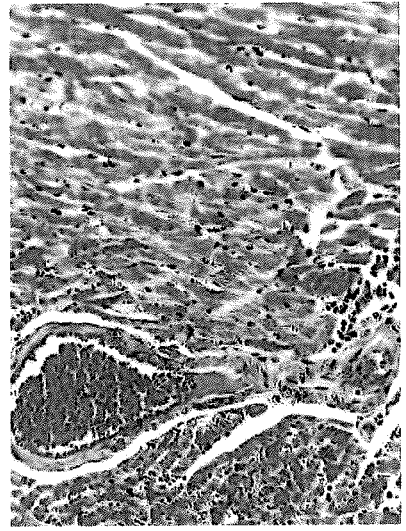
Figure 10E:
Figure 10F:
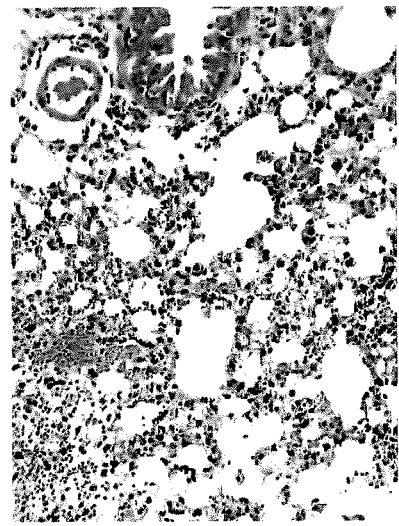
Figure 10G:
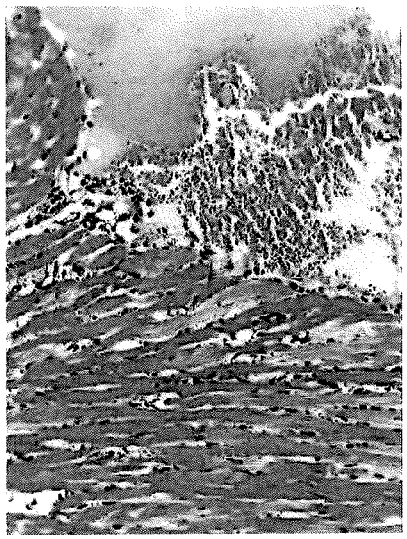
Figure 10H:
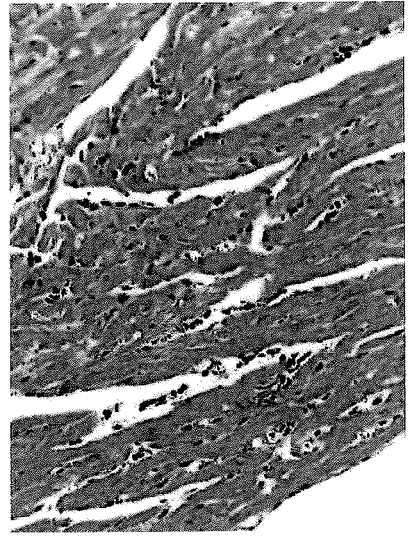
Figure 10I:
Figure 10J:
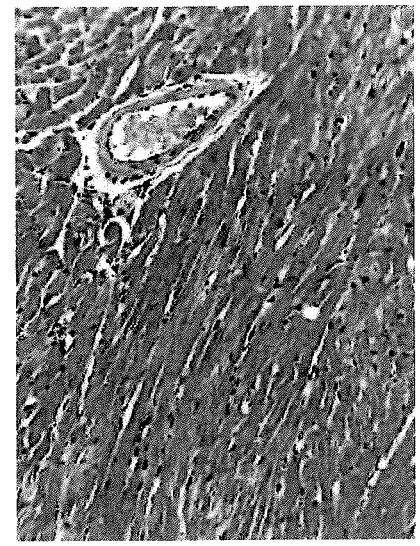

The H&E-stained heart sections of the control group revealed normal histological morphology, as well as normal features of myocardial cells and blood vessels (See FIGS. 10A and 10B). When tissue sections from *A. fumigatus*-infected mice were compared to those from the non-infected control group, serious pathological aberrations were identified in the *A. fumigatus*-infected group's cardiac tissues (See FIGS. 10C and 10D). Loss of typical muscle fiber architecture, loss of cross striations, and fragmentation of sarcoplasm were observed in the *A. fumigatus* infected group, along with irregular foci of extravasated erythrocytes scattered within the myocardium accompanied by other histopathologic manifestations of myocardial damage. Additionally, a few scattered foci of inflammatory infiltration are consistent with myocyte degeneration. Intense cytoplasmic eosinophilia was noted in necrotic myocytes, which was coupled with nuclear pyknosis or even karyolysis. Compared with the *A. fumigatus* infected group, the above changes were comparable in groups treated with fluconazole or dabigatran etexilate alone. However, when compared to non-treated *A. fumigatus* infected mice, the histologic findings in the fluconazole and dabigatran etexilate combination were significantly improved, despite a mild histologic change in the myocardial tissues in the treated groups in the form of degenerative changes in myocardial fibers with congested blood vessels (See FIGS. 10E-10J). Furthermore, there was no evident inflammatory reaction, and there was considerably reduced cardiomyocyte necrosis, apoptosis, myomalacia, and myocytolysis.

Histopathological Evaluation of Systemic Aspergillosis: Lung

Figure 11A:
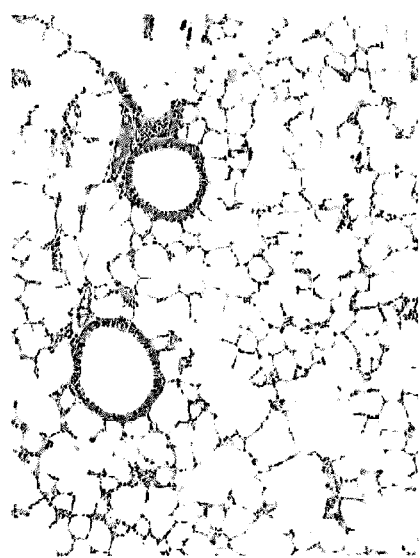
FIGS. 11A-11J depict histopathological examination of lung sections of healthy control mice (11A-11B), of mice infected with *A. fumigatus* (11C-11D), of mice infected with *A. fumigatus* and treated with fluconazole (11E-11F), of mice infected with *A. fumigatus* and treated with dabigatran etexilate (11G-11H), and of mice infected with *A. fumigatus* and treated with both fluconazole and dabigatran etexilate 11I-11J). (10×=11A, 11C, 11E, 11G, 11I 40×=11B, 11D, 11F, 11H, 11J)
Figure 11B:
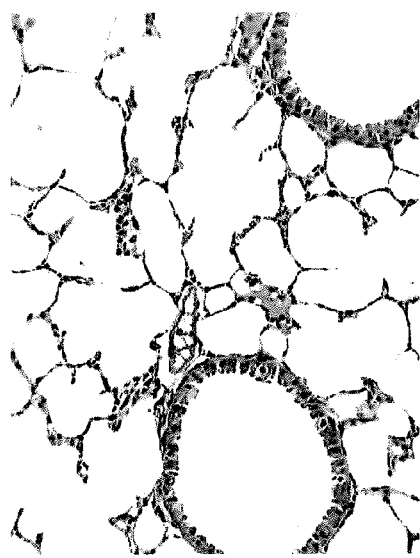
Figure 11C:
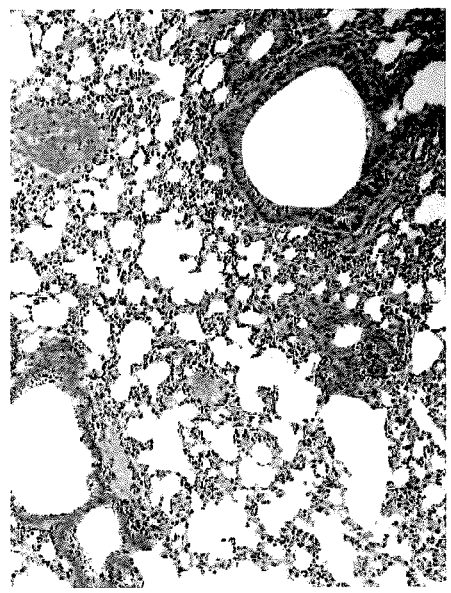
Figure 11D:
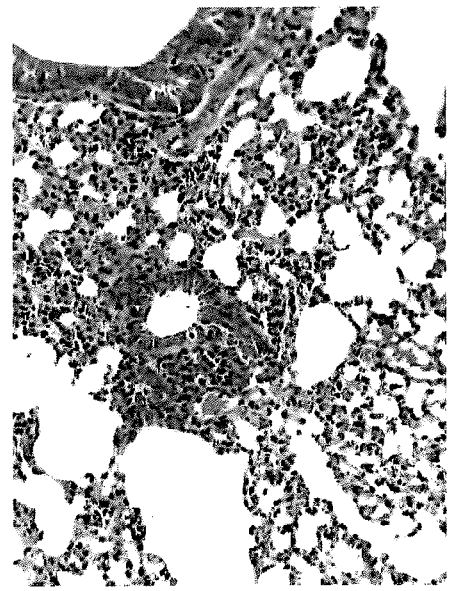
Figure 11E:
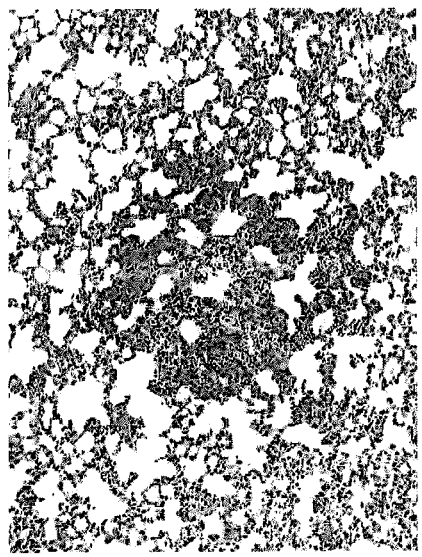
Figure 11F:
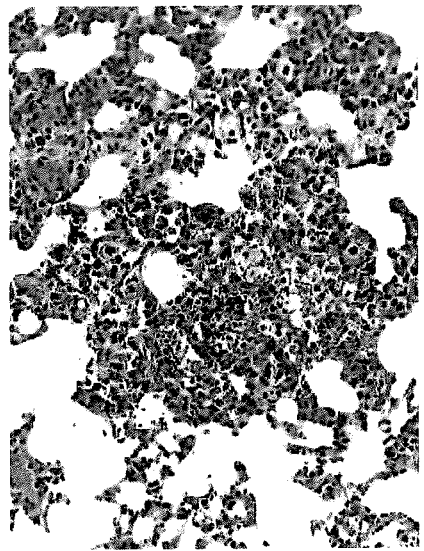
Figure 11G:
Figure 11H:
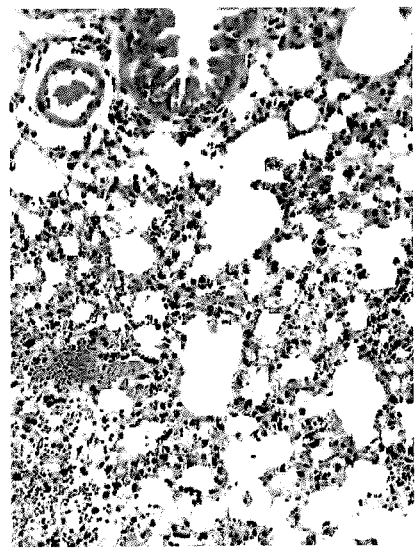
Figure 11I:
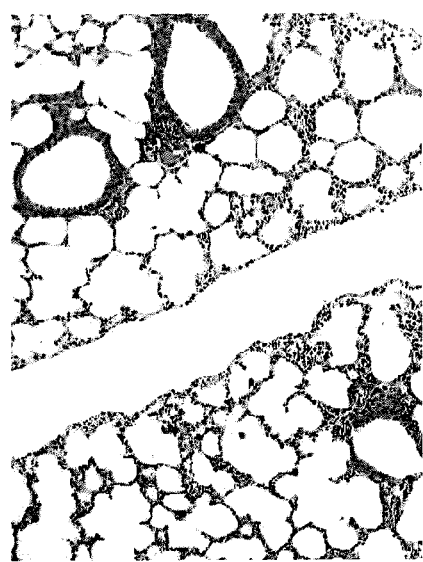
Figure 11J:
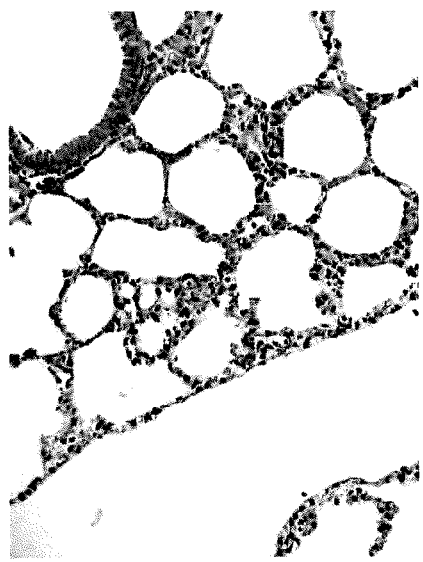

Lungs of control rats were shown to have normal histologic spongy architecture, with no inflammatory cell infiltration and no apparent damage to the alveoli, including the alveolar sacs, the alveoli, the respiratory trachea, and the blood vessels (See FIGS. 11A and 11B). In contrast, pulmonary sections of mice infected with *A. fumigatus* were consolidated with a thickened alveolar wall, congested blood vessels, and inflammatory cell infiltration. Occasionally, non-necrotizing granulomatous reactions were located near the larger airways. The affected regions were found close to minimally affected or even normal regions. In this respect, the granulomatous lesion was then consolidated and localized (See FIGS. 11C and 11D). In the fluconazole sections, inflammation was similar in character but slightly less severe, with less localization and less inflammatory response consolidation (See FIGS. 11E and 11F). In the fluconazole and dabigatran etexilate sections, the inflammation was scattered and much less pronounced; however, treatment with dabigatran etexilate showed decreased airspace areas because of red blood cells extravasation. Combination with fluconazole reduced this effect (See FIGS. 11G-11J).

Histopathological Evaluation of Systemic Aspergillosis: Kidney

Figure 12A:
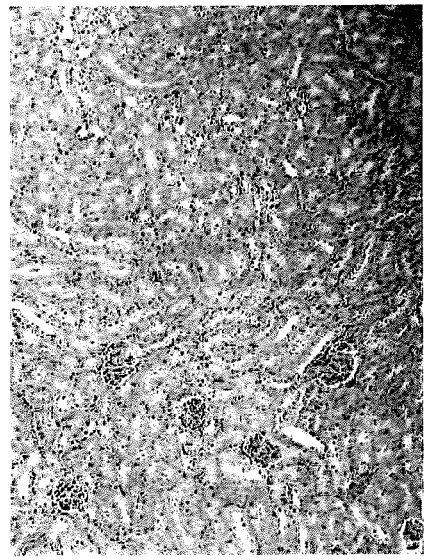
FIGS. 12A-12J depict histopathological examination of kidney sections of healthy control mice (12A-12B), of mice infected with *A. fumigatus* (12C-12D), of mice infected with *A. fumigatus* and treated with fluconazole (12E-12F), of mice infected with *A. fumigatus* and treated with dabigatran etexilate (12G-12H), and of mice infected with *A. fumigatus* and treated with both fluconazole and dabigatran etexilate (12I-12J). (10×=12A, 12C, 12E, 12G, 12I 40×=12B, 12D, 12F, 12H, 12J)
Figure 12B:
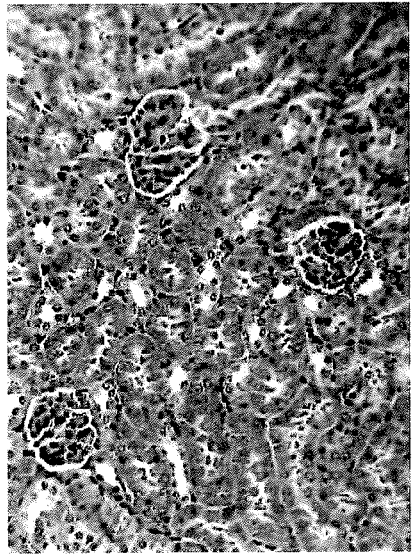
Figure 12C:
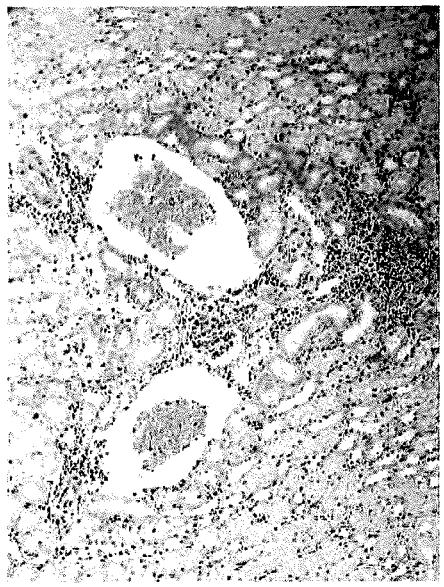
Figure 12D:
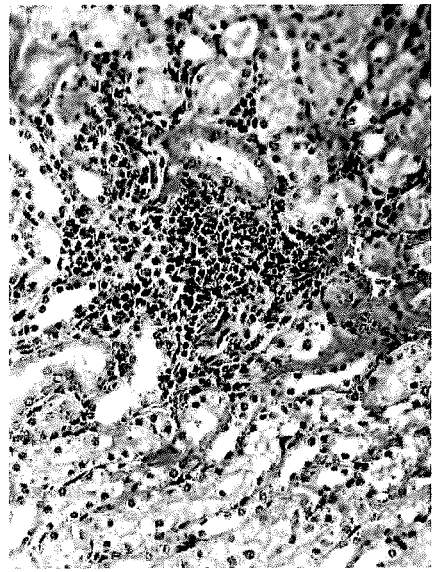
Figure 12E:
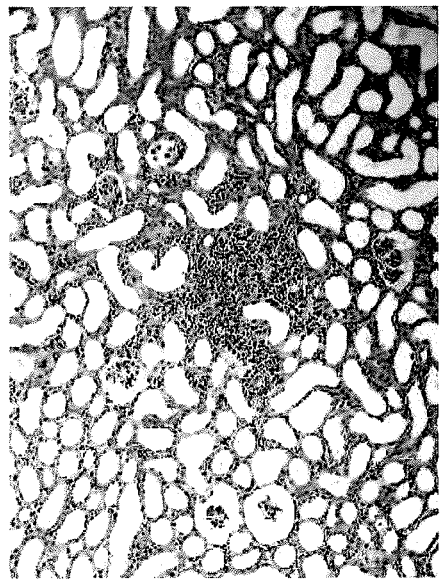
Figure 12F:
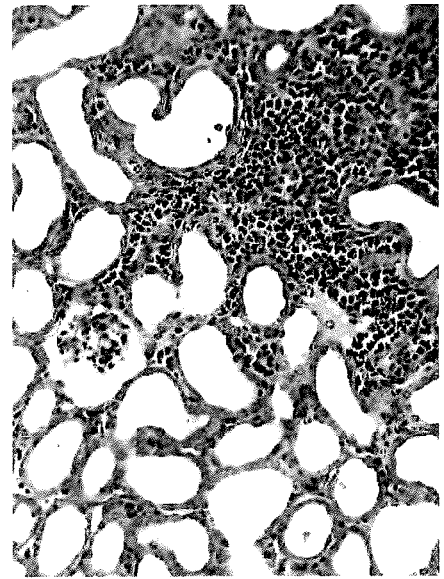
Figure 12G:
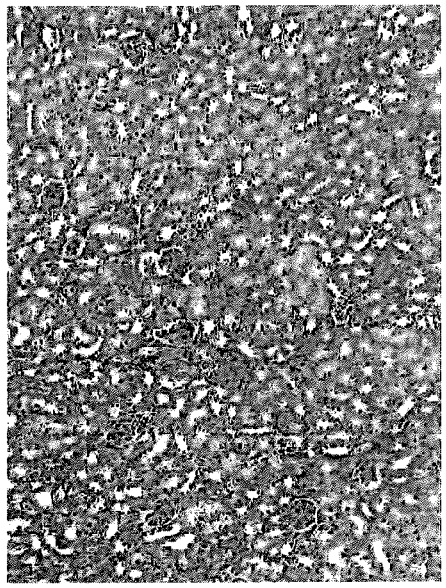
Figure 12H:
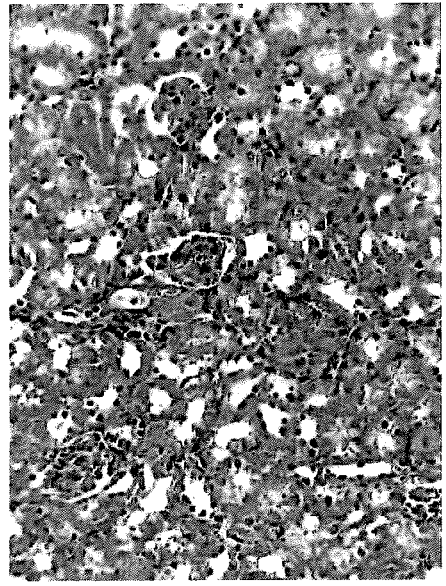
Figure 12I:
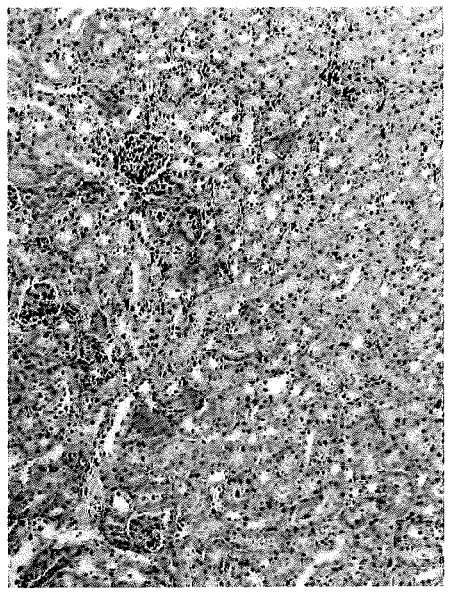
Figure 12J:
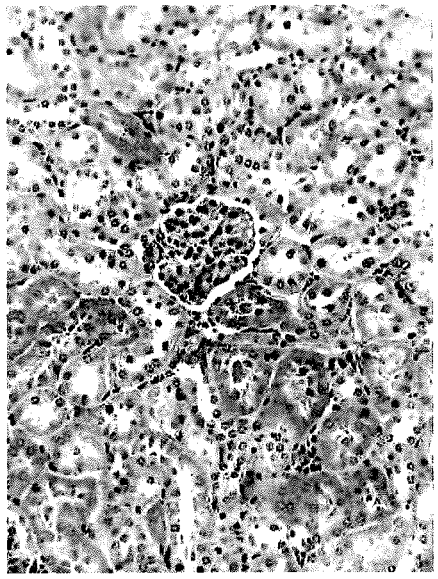

Renal histopathology in control mice revealed no structural changes in the cortical and medullary interstitial tissue, as well as normal glomeruli surrounded by normal tubules (See FIGS. 12A and 12B). Tubulonephrosis, characterized by focal interstitial inflammation, focal mild tubular injury in the adjacent tubules, tubular dilation, and extravasated RBCs, was evident in *A. fumigatus* infected animals (See FIGS. 12C and 12D). Fluconazole treatment resulted in similar histological alterations. However, tubular dilation in this group was diffused with visible intraluminal protein cast. Many histological aspects of the kidneys in mice infected with *A. fumigatus* and treated with dabigatran etexilate alone or in combination with fluconazole showed modest improvements, including the absence of inflammatory cells but with mild tubular disruption (See FIGS. 12E-12J).

Example 4

In Vivo Vaginal Antifungal Assays

Vaginal Candidiasis

Figure 13:
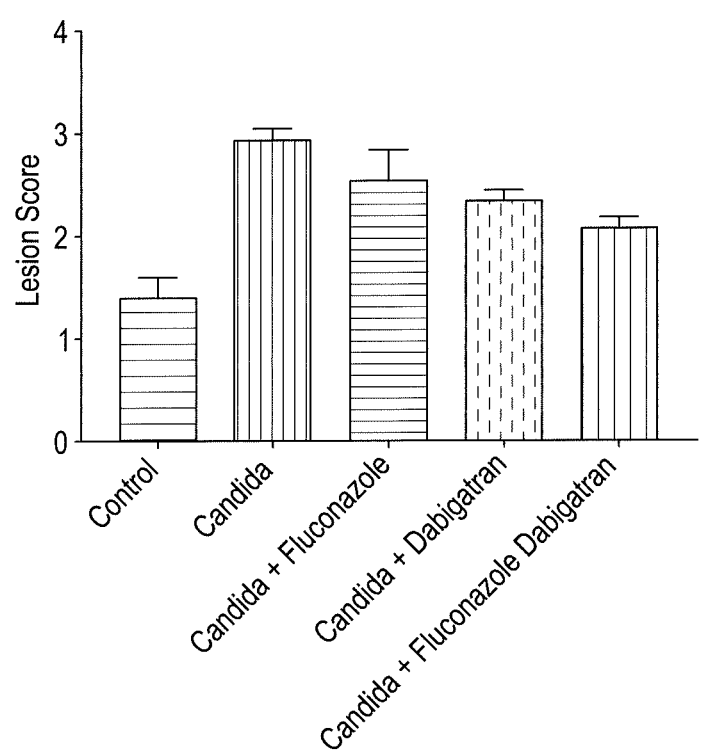
FIG. 13 depicts a graph of lesion score of mouse vagina for control non-treated animals, *C. albicans* injected without therapy, and *C. albicans* infected and treated with fluconazole, dabigatran, or fluconazole and dabigatran etexilate combination.

Mice vagina infected with *C. albicans* was used to evaluate the anticandidal actions of dabigatran. To help in induction of vaginal candidiasis, mice were immunocompromised by injection of 0.1 mg of β-estradiol in 10 μl of sesame oil 72 h and 24 h before vaginal infection for induction of estrus. Infection was done during the estrus phase by intravaginal dropping of the *Candida* blastoconidia. Each mouse received $3\times10^6$ blastospores into the vaginal cavity. Uninoculated control mice (the control group) were injected intravaginally with sterile saline. Five groups of eight mice were allocated as follows: 1—non-infected non-treated control group, 2—infected with *Candida* without treatment, 3—infected with *Candida* and treated with fluconazole, 4—infected with *Candida* and treated with dabigatran etexilate, and 5—infected with *Candida* and treated with fluconazole+dabigatran etexilate combination. All drugs were given topically into the vagina at a dose rate of 5 mg/kg daily for seven days post-infection. On the seventh day, the mice were sacrificed, and blood and vaginal samples were collected. A summary of the data collected is provided in FIG. 13.

H&E Stain

At ×400 magnification, five visual random fields were analyzed. An adopted procedure was used to assess the degree of infection and inflammation (Zhang, J. E., et al., "Feasibility of histological scoring and colony count for evaluating infective severity in mouse vaginal candidiasis," Experimental Animals, 62(3): pp. 205-10 (2013)). The average scores of five fields were recorded. All treatments significantly improved vaginal candidiasis scores. (See Table 3)

TABLE 3

Vaginal Lesion Scoring System Used to Evaluate the Effect of Dabigatran Etexilate in Relieving Vaginal Candidiasis (Scores 0-3) (Modified Scores 1-4)

| Extent | Score | Modified score | Epithelial layer | Submucosa |
|---|---|---|---|---|
| Absent | Score 0 | Score 1 | No neutrophils | No neutrophils |
| Mild | Score 1 | Score 2 | 1-10 neutrophils or 1-3 microabscesses | Few neutrophils |
| Moderate | Score 2 | Score 3 | 11-20 neutrophils or 4-6 microabscesses | some neutrophils |
| Severe | Score 3 | Score 4 | >20 neutrophils or >6 microabscesses | numerous neutrophils |

Figure 14A:
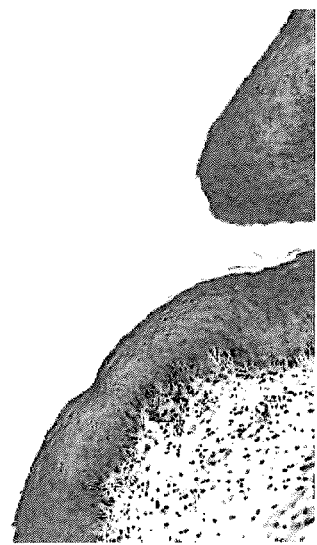
Figure 14B:
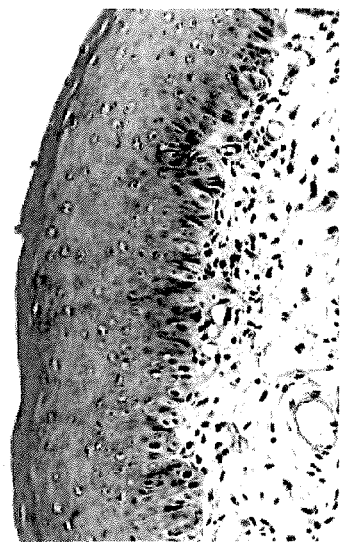
Figure 14C:
Figure 14D:
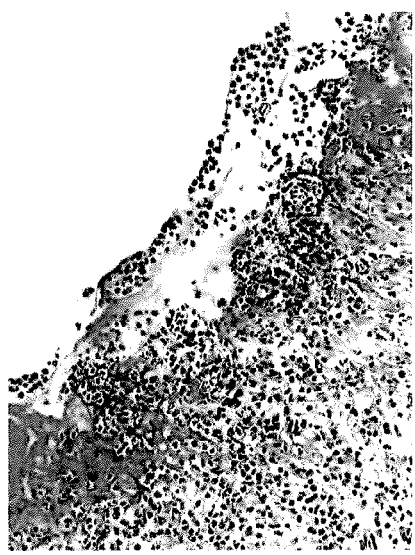
Figure 14E:
Figure 14F:
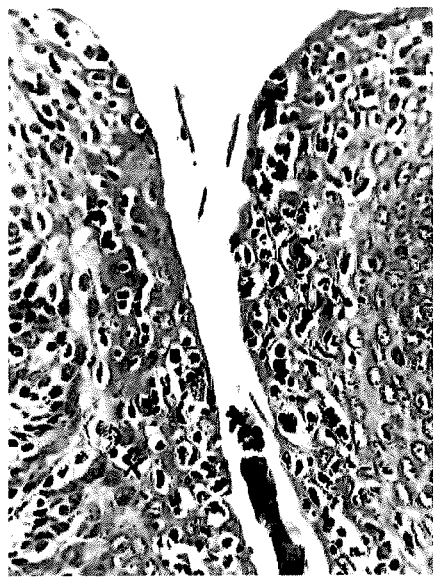
Figure 14G:
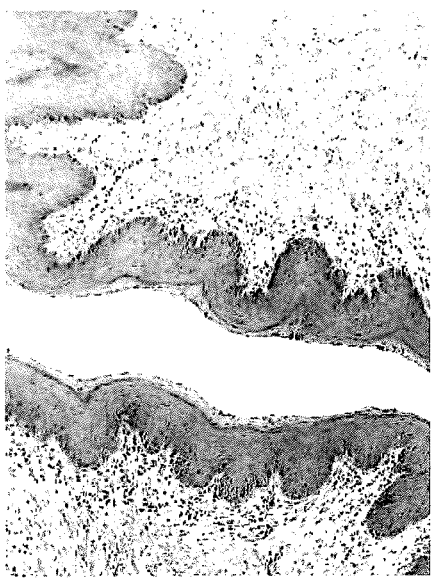
Figure 14H:
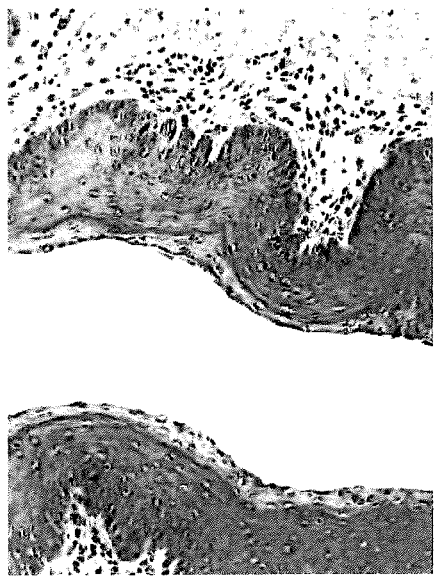
Figure 16A:
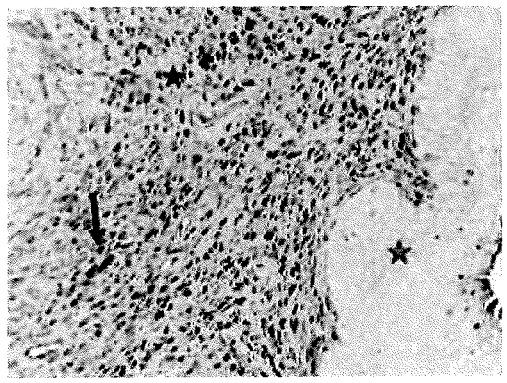
FIGS. 16A-16B depict photomicrographs (20×=16A, 40×=16B) of Immunohistochemical staining of CD45 in *C. albicans* infected mice vaginal tissue. CD4+ cells in infection foci were detected using anti-CD4 Ab by IHC. Examples of CD45-positive cell dye are indicated by black arrows; Notice migration of CD4+ cells to the vaginal lamina propria of infected mice. Stratified squamous epithelium (red star). Underlying lamina propria (blue star).
Figure 16B:
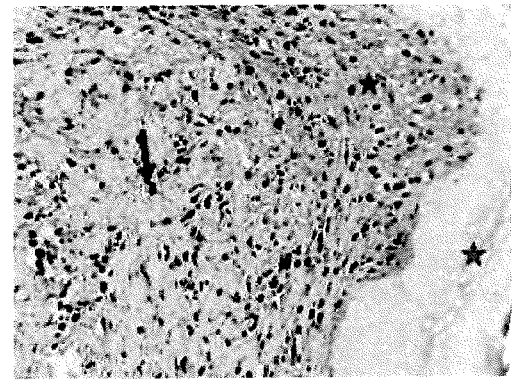
Figure 17A:
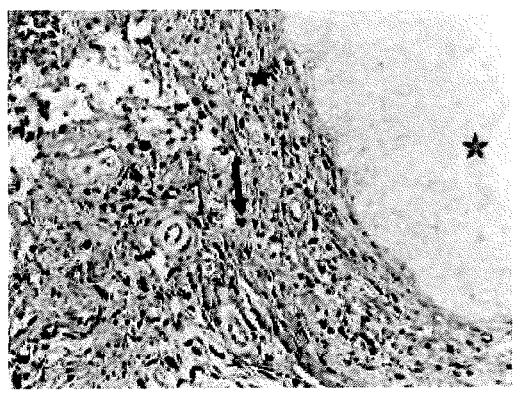
FIGS. 17A-17B depict photomicrographs (20×=17A, 40×=17B) of Immunohistochemical staining of CD45 in *C. albicans* infected and treated by fluconazole mice vaginal tissue. CD4+ cells in infection foci were detected using anti-CD4 Ab by IHC. Examples of CD45-positive cell dye are indicated by black arrows; Notice migration of CD4+ cells to the vaginal lamina propria of infected mice. Stratified squamous epithelium (red star). Underlying lamina propria (blue star).
Figure 17B:
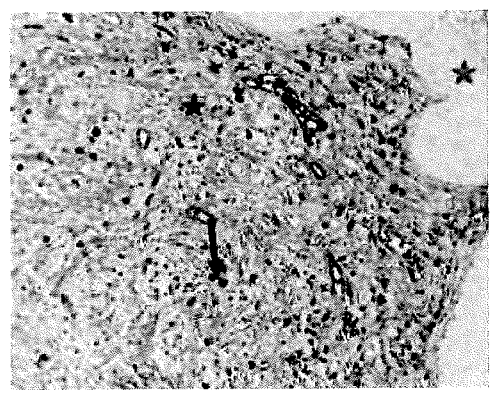

Light microscopy was used to evaluate the histological features of *C. albicans* vaginal infection as well as the efficacy of dabigatran etexilate treatment. The non-infected control animals had typical vaginal mucosa morphology, consisting of stratified squamous epithelium resting on dense sub-epithelial connective tissue and showing no symptoms of inflammation (See FIGS. 14A and 14B). In contrast, infected control mice displayed certain histological abnormalities, including exfoliation of epithelial cells, subcorneal microabscesses, necrosis, and ulceration (See FIGS. 14 C and 14D). On the other hand, fluconazole treatment showed a modest sub-epithelial inflammatory reaction with intact mucosa still showing keratin layer breakdown and neutrophils infiltrating the epithelium (See FIGS. 14E and 14F). In comparison to the mucosa of the control animals, animals infected with *Candida* and treated with dabigatran etexilate for 7 days showed a considerable reduction in inflammation and injury to the vaginal epithelial mucosa. Furthermore, treatment with fluconazole+dabigatran etexilate resulted in almost full mucosal healing, with only little neutrophils remaining in the epithelium and lamina propria with mildly dispersed sub-epithelial connective tissue and dilated blood vessels due to edema (See FIGS. 14G-14J).

Mouse Vagina CD45 (Common Leukocyte Antigen)

CD45 (common leukocyte antigen) is a marker for immune cells expressed primarily by hematopoietic cells other than erythrocytes and plasma cells. CD45's number and distribution were semi-quantitatively investigated with IHC test to find out if the antifungal treatment decreased the penetration of inflammatory immune cells into the vaginal mucosa. All treated groups showed that the immune cell allocation was the same as that of control tissues, with CD45-positive cells scattered throughout the submucosa. CD45-positive cells were observed massively infiltrated in the vaginal tissue of the C. albicans infected Model animals straight below the basal cell layer. CD45 positives did not, however, coincide with disruption of the epithelium. Mild to moderate CD45-positive cells spread across the submucosa were observed in dabigatran etexilate and fluconazole-treated animals. However, there were no substantial changes in the distribution of immune cells in the vaginal mucosa between the different treatment groups (See FIGS. 15A-15B, 16A-16B, 17A-17B, 18A-18B, and 19A-19B).

CXCR4 Protein Expression

Figure 20A:
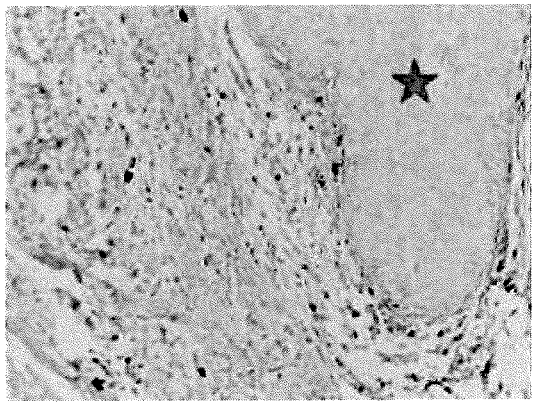
FIGS. 20A-20B depict photomicrographs (10×=20A, 20×=20B) of Immunohistochemical staining of CXCR4 in control mice vaginal tissue. Negative ICH staining of vaginal stratified squamous epithelium (red star).
Figure 20B:
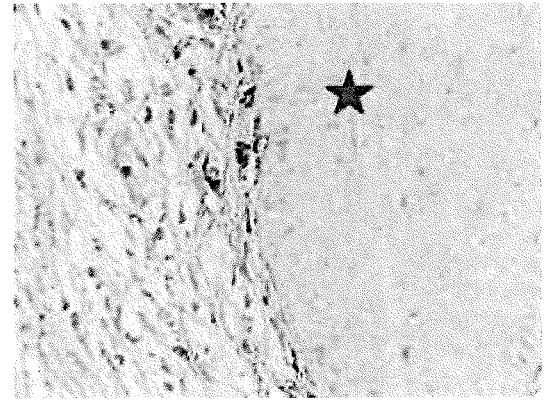
Figure 21A:
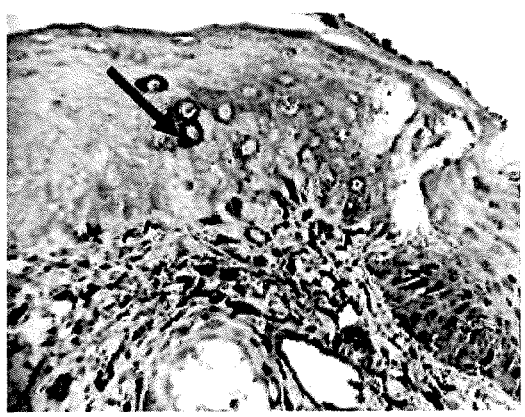
FIGS. 21A-21B depict photomicrographs (20×=21A, 40×=21B) of Immunohistochemical staining of CXCR4 in *C. albicans* infected mouse vaginal tissue. Weak or strong staining was recognized as low or high CXCR4 expression, which mainly appear as brown particles in the keratinocyte cell membrane and cytoplasm. Further expression in the cytoplasm of some inflammatory cells is found in both lamina propria.
Figure 21B:
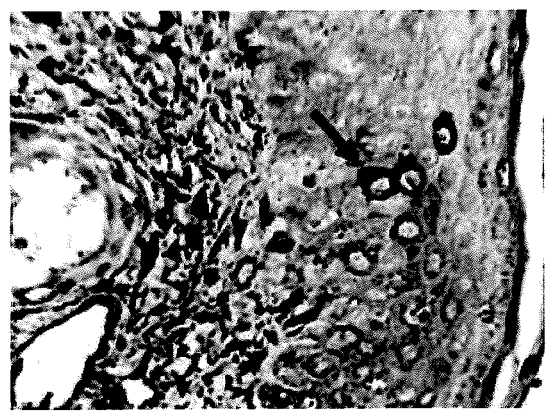
Figure 22A:
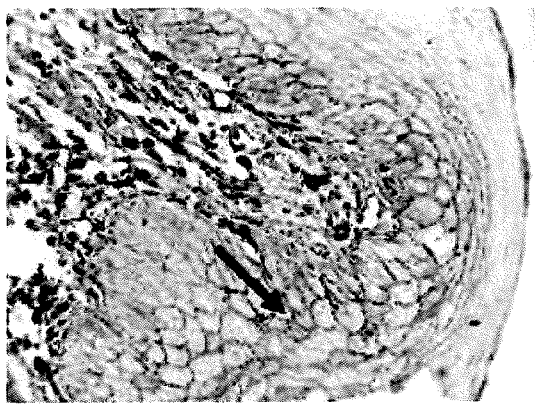
FIGS. 22A-22B depict photomicrographs (20×=22A, 40×=22B) of Immunohistochemical staining of CXCR4 in *C. albicans* infected and treated by fluconazole mouse vaginal tissue. Weak or strong staining was recognized as low or high CXCR4 expression, which mainly appear as brown particles in the keratinocyte cell membrane and cytoplasm. Further expression in the cytoplasm of some inflammatory cells found in both lamina propria.
Figure 22B:
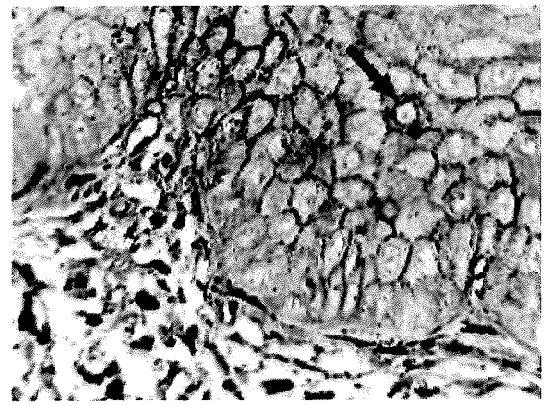
Figure 23A:
FIGS. 23A-23B depict photomicrographs (10×=23A, 20×=23B) of Immunohistochemical staining of CXCR4 in *C. albicans* infected and fluconazole+dabigatran etexilate treated mouse vaginal tissue. Mice in the fluconazole+dabigatran etexilate treated group exhibited almost no apparent cells with a positively-expressed CXCR4.
Figure 23B:
Figure 24A:
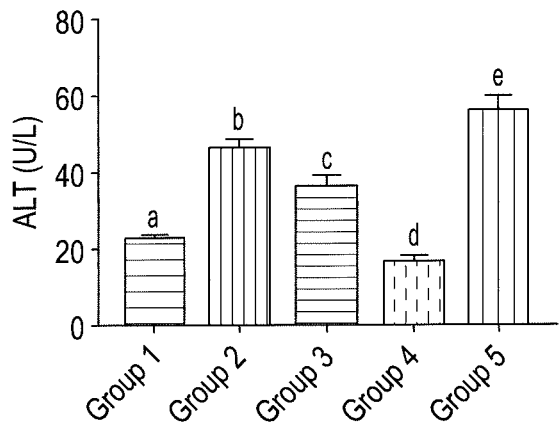
FIGS. 24A-24D depict graphs of the serum levels of ALT, AST, uric acid, and creatinine in mice infected with systemic candidiasis. Group 1: Noninfected non treated control, Group 2: Infected with *Candida* without treatment, Group 3: Infected with *Candida* and treated with fluconazole, Group 4: Infected with *Candida* and treated with dabigatran etexilate, Group 5: Infected with *Candida* and treated with fluconazole+dabigatran etexilate combination. Mean values in each plot followed by a different lowercase letter (a, b, c) are significantly different at p≤0.05.
Figure 24B:
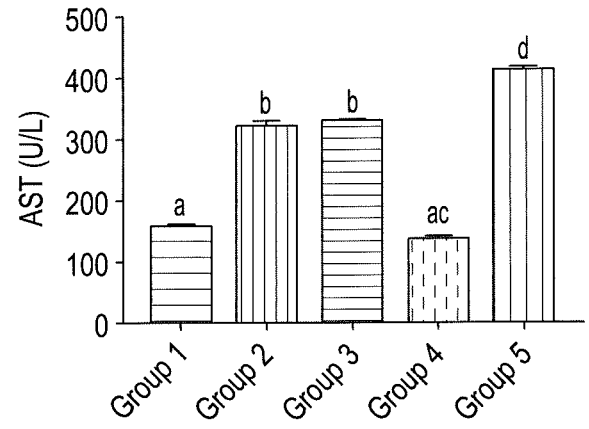
Figure 24C:
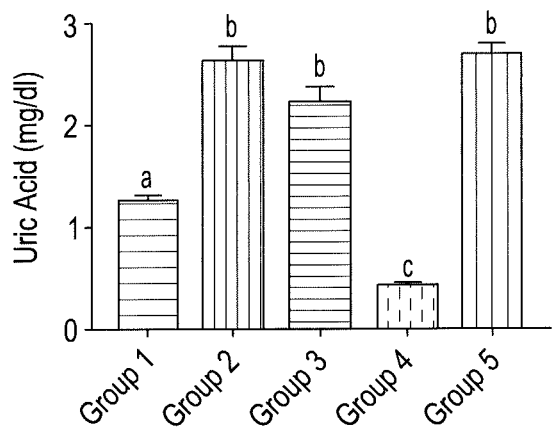
Figure 24D:
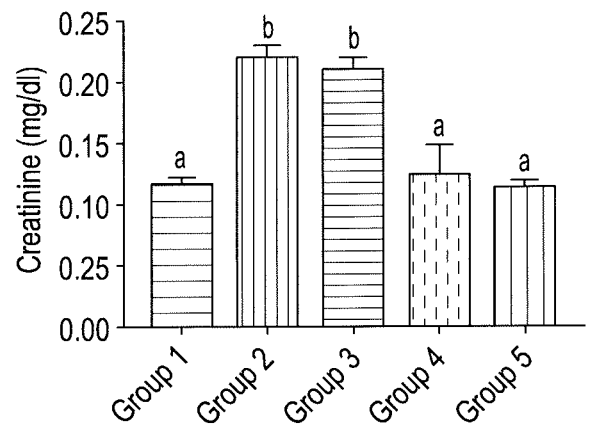
Figure 25A:
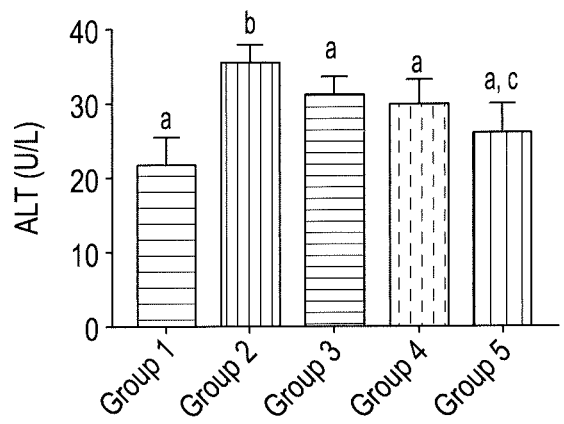
FIGS. 25A-25D depict graphs of the serum levels of ALT, AST, uric acid, and creatinine in mice infected with vaginal candidiasis. Group 1: Non infected non treated control, Group 2: Infected with *Candida* without treatment, Group 3: Infected with *Candida* and treated with fluconazole, Group 4: Infected with *Candida* and treated with dabigatran etexilate, Group 5: Infected with *Candida* and treated with fluconazole+dabigatran etexilate combination. Mean values in each plot followed by a different lowercase letter (a, b, c) are significantly different at p≤0.05.
Figure 25B:
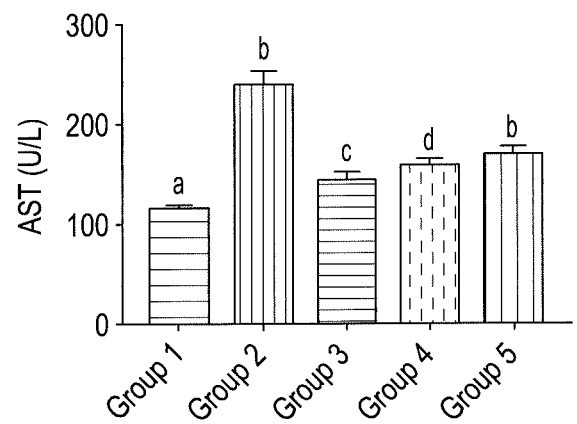
Figure 25C:
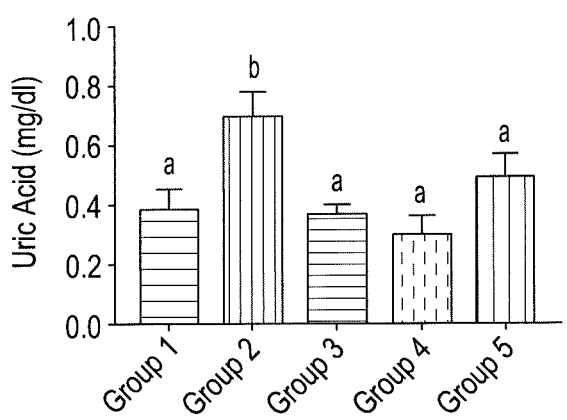
Figure 25D:
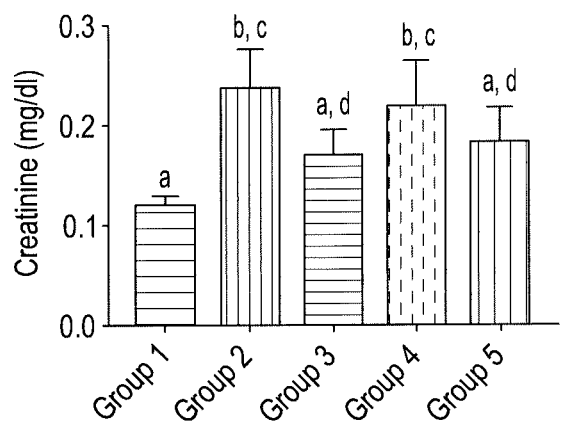
Figure 26A:
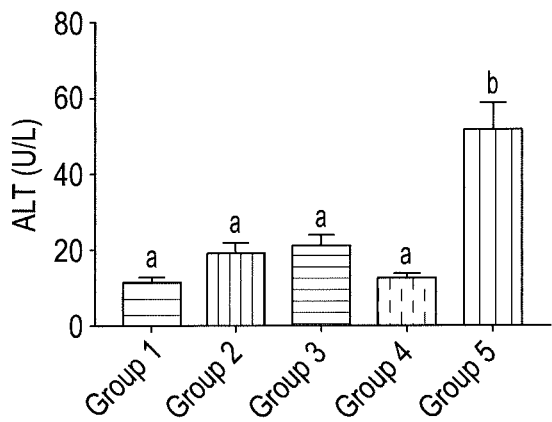
FIGS. 26A-26D depict graphs of the serum levels of ALT, AST, uric acid, and creatinine in mice infected with vaginal candidiasis. Group 1: Non-infected, non-treated control, Group 2: Infected with *Candida* without treatment, Group 3: Infected with *Candida* and treated with fluconazole, Group 4: Infected with *Candida* and treated with dabigatran etexilate, Group 5: Infected with *Candida* and treated with fluconazole+dabigatran etexilate combination. Mean values in each plot followed by a different lowercase letter (a, b, c) are significantly different at p≤0.05.
Figure 26B:
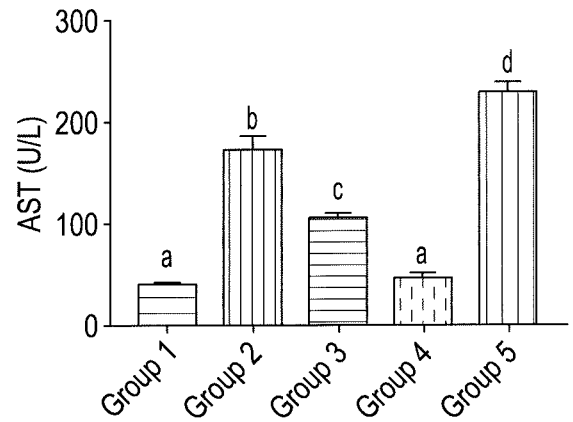
Figure 26C:
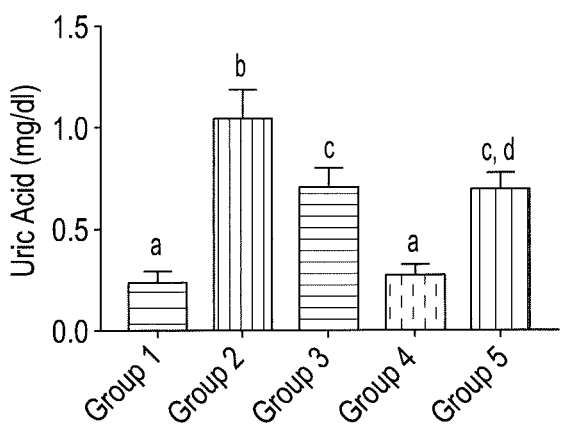
Figure 26D:
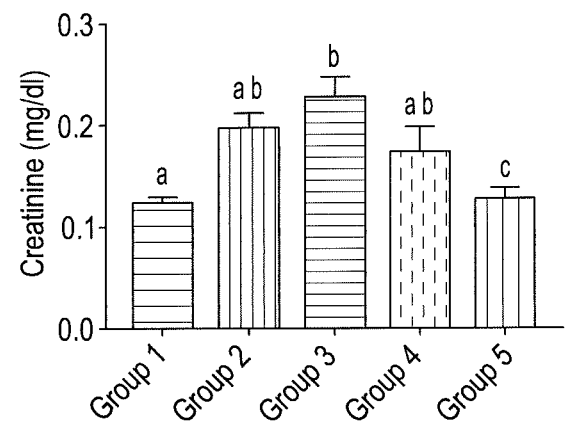

Immunohistochemical staining was conducted to identify positive CXCR4 protein expression. The appearance of brown particles showed the positive expression of CXCR4 protein (See FIGS. 20A and 20B). In the vaginal mucosa of the mice in the control group, no CXCR4 expression was apparent. In contrast, the CXCR4 protein in vaginal tissues of the C. albicans infected Model animals showed predominantly expressed protein in keratinocyte cell membrane and cytoplasm (See FIGS. 21A and 21B). In addition, CXCR4 has been further expressed in the cytoplasm of some inflammatory cells found in both lamina propria as well as vascular endothelial cells. Animals Injected with C. albicans and treated with fluconazole or dabigatran etexilate for 7 days demonstrated a significant decrease of CXCR4 expression in the vaginal epithelial mucosa in comparison with the C. albicans infected Model animals' mucosa. Moreover, treatment with fluconazole+dabigatran etexilate led to a substantial reduction of CXCR4 expression in the lamina propria of the vaginal submucosa relative to C. albicans infected Model animals' submucosa (See FIGS. 22A, 22B, 23A, 23B).

Example 5

Serum Chemistry from In Vivo Systemic and Vaginal Antifungal Assays

Serum Chemistry: Systemic Candidiasis

Serum samples from the systemic candidiasis experiments discussed above were analyzed using known techniques to detect serum levels of ALT, AST, uric acid, and creatinine.

Systemic infection with C albicans led to increased serum levels of ALT, AST, uric acid, and creatinine (See FIGS. 24A-24D). Compared with the infected nontreated group (Group 2), treatment with fluconazole had led to a significant decrease in ALT levels only. In contrast, dabigatran etexilate significantly decreased all serum markers. Interestingly, Group 5 which received combined fluconazole and dabigatran etexilate treatment showed a significant increase in ALT, AST, and uric acid, compared with both the control noninfected and infected nontreated groups (See FIGS. 24A-24D). Despite the observed improvement in organ pathological changes in Group 5, compared with other groups, this combination showed increased liver enzymes ALT and AST levels.

Serum Chemistry: Vaginal Candidiasis

Serum samples from the vaginal candidiasis experiments discussed above were analyzed using known techniques to detect serum levels of ALT, AST, uric acid, and creatinine.

Vaginal infection with C albicans also led to increased serum levels of ALT, AST, uric acid, and creatinine (See FIGS. 25A-25D). Compared with the infected nontreated group (Group 2), all treatments had led to a significant decrease in ALT, AST, uric acid, and creatinine.

Serum Chemistry: Systemic Aspergillus Infection

Serum samples from the systemic Aspergillus experiments discussed above were analyzed using known techniques to detect serum levels of ALT, AST, uric acid, and creatinine.

Systemic infection with A. fumigatus led to increased serum levels of AST, uric acid, and creatinine (See FIGS. 26A-26D). Compared with the infected nontreated group (Group 2), treatment with fluconazole had led to a significant decrease in all markers, except creatinine. Dabigatran etexilate significantly decreased all serum markers. Similar to systemic candidiasis, Group 5 which received combined fluconazole and dabigatran etexilate treatment showed a significant increase in ALT, AST, and uric acid, compared with both the control noninfected and infected nontreated groups.

It is to be understood that the treatment of fungal infections using dabigatran etexilate is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating a fungal infection, comprising administering a therapeutically effective amount of dabigatran etexilate to a subject in need thereof.

2. The method of claim 1, wherein the dabigatran etexilate is administered to treat a topical infection.

3. The method of claim 1, wherein the dabigatran etexilate is administered to treat a systemic infection.

4. The method of claim 1, wherein the dabigatran etexilate is administered as part of a pharmaceutical composition.

5. The method of claim 4, wherein the pharmaceutical composition is formulated for oral administration.

6. The method of claim 1, wherein the fungal infection is caused by a fungal pathogen selected from the group consisting of *Aspergillus flavus, Aspergillus fumigatus, Aspergillus nidulans, Aspergillus niger, Aspergillus terreus, Aspergillus ustus, Candida albicans, Candida alibicans, Candida glabrata, Candida lipolytica, Candida tropicalis, Candida tropicalis, Cryptococcus neoformans, Cryptococcus neoformas, Fusarium moniliforme, Geotricum candidum, Microsporum canis, Mucor circillelloides, Penicillium aurantiogriseum, Penicillium expansum, Penicillium italicum, Penicillium marneffei, Penicllium marneffeii, Rhizopus oryzaee, Sporotlirix schenckii, Syncephalastrum racemosum, Trichophyton mentagrophytes, Trichophyton rubrum*, and a combination thereof.

7. The method of claim 6, wherein the fungal infection is caused by *Candida albicans*.

8. The method of claim 6, wherein the fungal infection is caused by *Aspergillus fumigatus*.

* * * * *